United States Patent
Nakazawa et al.

(10) Patent No.: US 11,154,206 B2
(45) Date of Patent: Oct. 26, 2021

(54) VISCOELASTICITY CHARACTERISTICS ACQUISITION DEVICE, VISCOELASTICITY CHARACTERISTICS ACQUISITION METHOD, VISCOELASTICITY CHARACTERISTICS ACQUISITION PROGRAM, AND RECORDING MEDIUM RECORDING SAID PROGRAM

(71) Applicant: HAMAMATSU PHOTONICS K.K., Hamamatsu (JP)

(72) Inventors: Tomoya Nakazawa, Hamamatsu (JP); Rui Sekine, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 772 days.

(21) Appl. No.: 15/739,906

(22) PCT Filed: Mar. 8, 2016

(86) PCT No.: PCT/JP2016/057205
§ 371 (c)(1),
(2) Date: Dec. 26, 2017

(87) PCT Pub. No.: WO2017/002401
PCT Pub. Date: Jan. 5, 2017

(65) Prior Publication Data
US 2018/0184922 A1    Jul. 5, 2018

(30) Foreign Application Priority Data
Jul. 1, 2015   (JP) .............................. JP2015-132527

(51) Int. Cl.
*A61B 5/02* (2006.01)
*A61B 5/021* (2006.01)
(Continued)

(52) U.S. Cl.
CPC .......... *A61B 5/02125* (2013.01); *A61B 5/022* (2013.01); *A61B 5/02007* (2013.01);
(Continued)

(58) Field of Classification Search
CPC .............. A61B 5/02125; A61B 5/7257; A61B 5/02108; A61B 5/022; A61B 5/14552;
(Continued)

(56) References Cited

U.S. PATENT DOCUMENTS 5,623,933 A * 4/1997 Amano .............. A61B 5/02007
600/500
2005/0277838 A1* 12/2005 Ikeda ................. A61B 5/02141
600/500
(Continued)

FOREIGN PATENT DOCUMENTS

CN          1251027 A     4/2000
CN        102481106 A     5/2012
(Continued)

OTHER PUBLICATIONS

International Preliminary Report on Patentability dated Jan. 11, 2018 for PCT/JP2016/057205.

*Primary Examiner* — Christian Jang
(74) *Attorney, Agent, or Firm* — Faegre Drinker Biddle & Reath LLP

(57) ABSTRACT

A viscoelastic characteristics acquisition device is a device that acquires viscoelastic characteristics of a blood vessel of an inspection target, and includes a pulse wave acquisition unit that acquires a time waveform corresponding to a volume pulse wave of the inspection target, a spectrum acquisition unit that acquires a volume pulse wave spectrum by performing Fourier transform on the time waveform, an input unit to which values corresponding to maximum blood pressure and minimum blood pressure of the inspection target are input, and an analysis unit that acquires the viscoelastic characteristics on the basis of the values corresponding to the maximum blood pressure and the minimum blood pressure and the volume pulse wave spectrum at a (Continued)

frequency equal to or higher than a frequency corresponding to the pulse of the inspection target.

13 Claims, 24 Drawing Sheets

(51) Int. Cl.
    *A61B 5/00*     (2006.01)
    *A61B 5/022*     (2006.01)
    *A61B 5/1455*     (2006.01)

(52) U.S. Cl.
    CPC ...... *A61B 5/02108* (2013.01); *A61B 5/14552* (2013.01); *A61B 5/6801* (2013.01); *A61B 5/7257* (2013.01); *A61B 5/0059* (2013.01); *A61B 5/6825* (2013.01); *A61B 5/6898* (2013.01); *Y10T 16/00* (2015.01)

(58) Field of Classification Search
    CPC . A61B 5/6801; A61B 5/02007; A61B 5/6825; A61B 5/0059; A61B 5/6898
    See application file for complete search history.

(56) References Cited

U.S. PATENT DOCUMENTS

| | | | |
|---|---|---|---|
| 2012/0253208 A1* | 10/2012 | Sawanoi | ................ G16H 50/30 600/490 |
| 2014/0288436 A1 | 9/2014 | Venkatraman et al. | |

FOREIGN PATENT DOCUMENTS

| | | |
|---|---|---|
| CN | 103156583 A | 6/2013 |
| CN | 103300820 A | 9/2013 |
| CN | 103648374 A | 3/2014 |
| CN | 104887195 A | 9/2015 |
| JP | H7-095966 A | 4/1995 |
| JP | 2002-325739 A | 11/2002 |
| JP | 2003-555 | 1/2003 |
| JP | 2004-121866 A | 4/2004 |
| JP | 2008-307307 A | 12/2008 |
| JP | 2010-017299 A | 1/2010 |
| JP | 2015-016350 A | 1/2015 |
| WO | WO-01/70106 A1 | 9/2001 |
| WO | WO-2014/129925 A1 | 8/2014 |

* cited by examiner

Fig.11
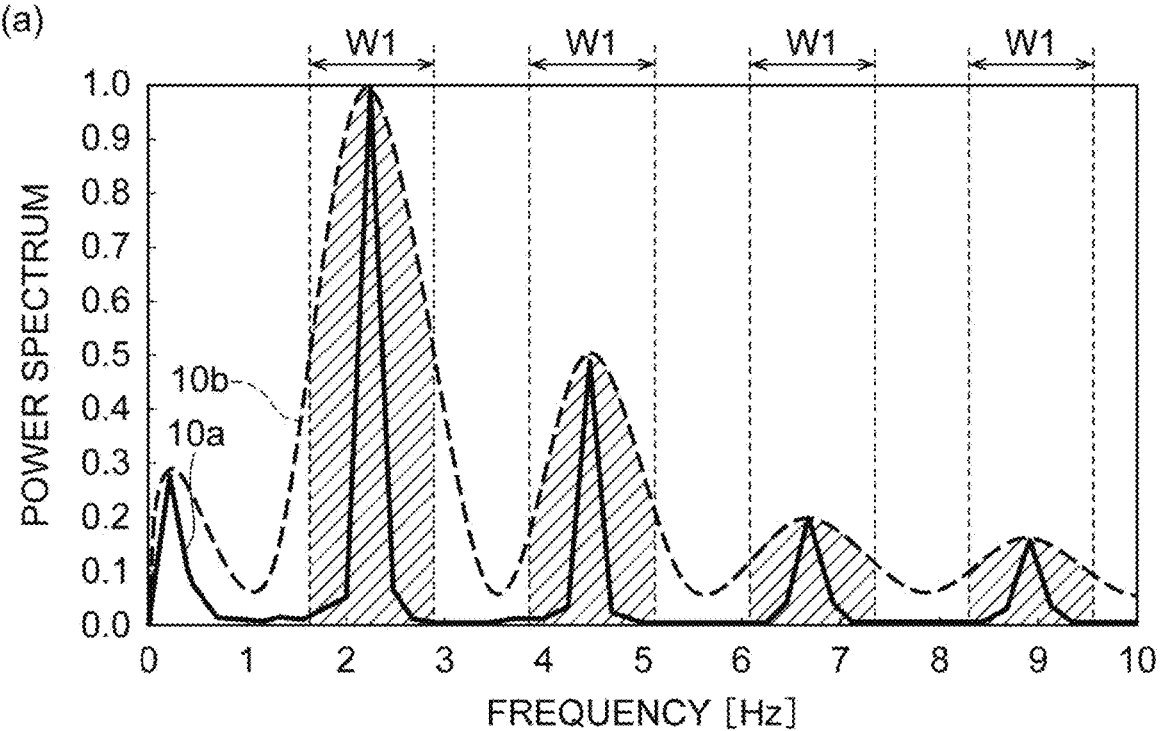
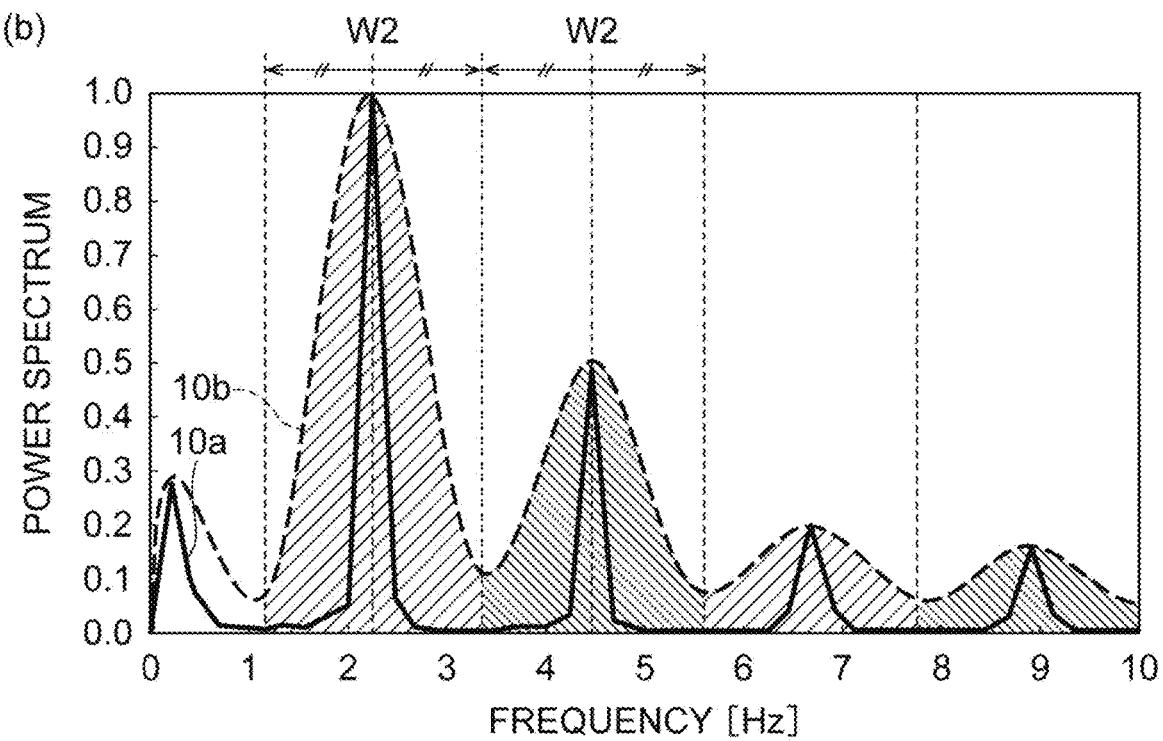

*Fig.20*
(a)
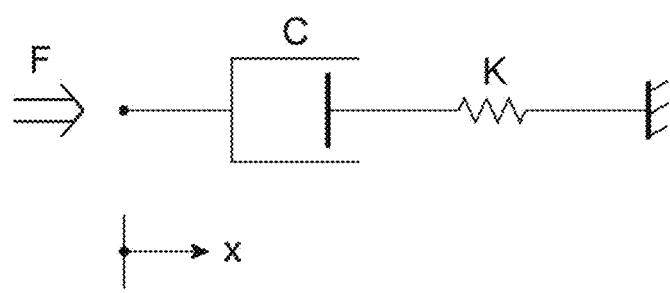
(b)
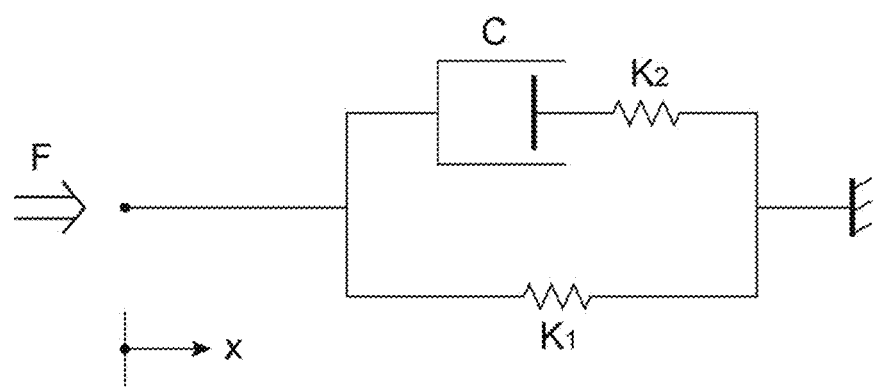

VISCOELASTICITY CHARACTERISTICS ACQUISITION DEVICE, VISCOELASTICITY CHARACTERISTICS ACQUISITION METHOD, VISCOELASTICITY CHARACTERISTICS ACQUISITION PROGRAM, AND RECORDING MEDIUM RECORDING SAID PROGRAM

TECHNICAL FIELD

An aspect of the present invention relates to a viscoelastic characteristics acquisition device, a viscoelastic characteristics acquisition method, a viscoelastic characteristics acquisition program, and a recording medium having the program recorded thereon.

BACKGROUND ART

In the related art, a method of measuring a blood pressure waveform by means of a tonometer method using a pressure pulse wave sensor is known. In the method of measuring the blood pressure waveform by means of the tonometer method, a relative change in arterial pressure can be measured, but it is difficult to accurately obtain an absolute pressure of the arterial pressure due to the viscoelastic nature of the skin and subcutaneous tissue. Therefore, it is necessary to calculate the absolute pressure of the arterial pressure by performing correction using a blood pressure value measured using a cuff. However, blood pressure waveform measurement using the tonometer method may not be able to be performed due to compression due to the cuff during the correction.

Thus, for example, in a blood pressure waveform monitoring device described in Patent Literature 1, an estimated blood pressure waveform is determined on the basis of a photoelectric pulse wave detected by a photoelectric pulse wave detection device instead of measuring the blood pressure waveform using the tonometer method during the above correction. Specifically, in the blood pressure waveform monitoring device, a relationship R between a pressure pulse wave PW acquired using a tonometer method and a photoelectric pulse wave LW is obtained in advance, and the estimated blood pressure waveform is acquired on the basis of the relationship R and the photoelectric pulse wave LW. Further, an estimated blood pressure waveform may be acquired using a transfer function H between the pressure pulse wave PW and the photoelectric pulse wave LW instead of the relationship R.

CITATION LIST

Patent Literature

[Patent Literature 1] Japanese Unexamined Patent Publication No. 2002-325739

SUMMARY OF INVENTION

As described in Patent Literature 1, when the relationship R between the pressure pulse wave PW acquired using the tonometer method and the photoelectric pulse wave LW is obtained, the device becomes large and is not convenient. Further, the transfer function H between the pressure pulse wave PW and the photoelectric pulse wave LW is determined on the basis of a known cardiovascular model, but a method of setting parameters in the cardiovascular model is unknown, and it is hard to say that the cardiovascular system can be evaluated sufficiently, and accurately.

An aspect of the present invention is to provide a viscoelastic characteristics acquisition device, a viscoelastic characteristics acquisition method, and a viscoelastic characteristics acquisition program capable of evaluating a cardiovascular system conveniently, sufficiently and accurately.

SUMMARY OF INVENTION

Technical Problem

As a result of intensive research, the present inventors have newly found that there is a statistically significant correspondence relationship between a spectrum at a frequency equal to or higher than a pulse frequency in a spectrum obtained as a result of performing Fourier transform on a blood pressure waveform and values corresponding to maximum blood pressure and minimum blood pressure. The present inventors have conceived that viscoelastic characteristics of the blood vessel can be derived on the basis of values corresponding to maximum blood pressure and minimum blood pressure of an inspection target and a volume pulse wave spectrum at a frequency equal to or higher than a frequency corresponding to the pulse of the inspection target on the basis of the finding that a volume pulse wave and a blood pressure waveform are associated on the basis of viscoelastic characteristics of the blood vessel, and the newly found correspondence relationship, thus completing an aspect of the present invention.

Solution to Problem

That is, an aspect of the present invention is a viscoelastic characteristics acquisition device for acquiring viscoelastic characteristics of a blood vessel of an inspection target, the viscoelastic characteristics acquisition device including: a pulse wave acquisition unit for acquiring a time waveform corresponding to a volume pulse wave of the inspection target; a spectrum acquisition unit for acquiring a volume pulse wave spectrum by performing Fourier transform on the time waveform; an input unit for inputting values corresponding to maximum blood pressure and minimum blood pressure of the inspection target; and an analysis unit for acquiring the viscoelastic characteristics on the basis of the values corresponding to the maximum blood pressure and the minimum blood pressure and the volume pulse wave spectrum at a frequency equal to or higher than a frequency corresponding to a pulse of the inspection target.

Further, another aspect of the present invention is a viscoelastic characteristics acquisition method of acquiring viscoelastic characteristics of a blood vessel of an inspection target, the viscoelastic characteristics acquisition method including: a pulse wave acquisition step of acquiring a time waveform corresponding to a volume pulse wave of the inspection target; a spectrum acquisition step of acquiring a volume pulse wave spectrum by performing Fourier transform on the time waveform; an input step of inputting values corresponding to maximum blood pressure and minimum blood pressure of the inspection target; and an analysis step of acquiring the viscoelastic characteristics on the basis of the values corresponding to the maximum blood pressure and the minimum blood pressure and the volume pulse wave spectrum at a frequency equal to or higher than a frequency corresponding to a pulse of the inspection target.

Further, still another aspect of the present invention is a program for causing a computer to execute viscoelastic characteristics acquisition for acquiring viscoelastic characteristics of a blood vessel of an inspection target, the program causing the computer to function as: a pulse wave acquisition unit for acquiring a time waveform corresponding to a volume pulse wave of the inspection target; a spectrum acquisition unit for acquiring a volume pulse wave spectrum by performing Fourier transform on the time waveform; an input unit for inputting values corresponding to maximum blood pressure and minimum blood pressure of the inspection target; and an analysis unit for calculating the viscoelastic characteristics on the basis of the values corresponding to the maximum blood pressure and the minimum blood pressure and the volume pulse wave spectrum at a frequency equal to or higher than a frequency corresponding to a pulse of the inspection target. Further, still another aspect of the present invention is a computer-readable recording medium having the viscoelastic characteristics acquisition program recorded thereon.

According to the viscoelastic characteristics acquisition device, the viscoelastic characteristics acquisition method, the viscoelastic characteristics acquisition program, and the recording medium having the program recorded thereon according to the above aspect of the present invention, the viscoelastic characteristics are acquired on the basis of the values corresponding to the maximum blood pressure and the minimum blood pressure of the inspection target, and the volume pulse wave spectrum at a frequency equal to or higher than the frequency corresponding to a pulse of the inspection target. Accordingly, it is possible to conveniently acquire highly accurate viscoelastic characteristics. The cardiovascular system can be evaluated on the basis of the viscoelastic characteristics.

Advantageous Effects of Invention

According to an aspect of the present invention, a viscoelastic characteristics acquisition device, a viscoelastic characteristics acquisition method, a viscoelastic characteristics acquisition program, and a recording medium having the program recorded thereon capable of evaluating a cardiovascular system conveniently, sufficiently, and accurately are provided.

BRIEF DESCRIPTION OF DRAWINGS

FIG. 11 is a diagram illustrating an effective width of the spectral intensity of the power spectrum illustrated in FIG. 10.

FIG. 20 is a diagram illustrating a series spring damper model and a series and parallel hybrid model.

DESCRIPTION OF EMBODIMENTS

Figure 1:
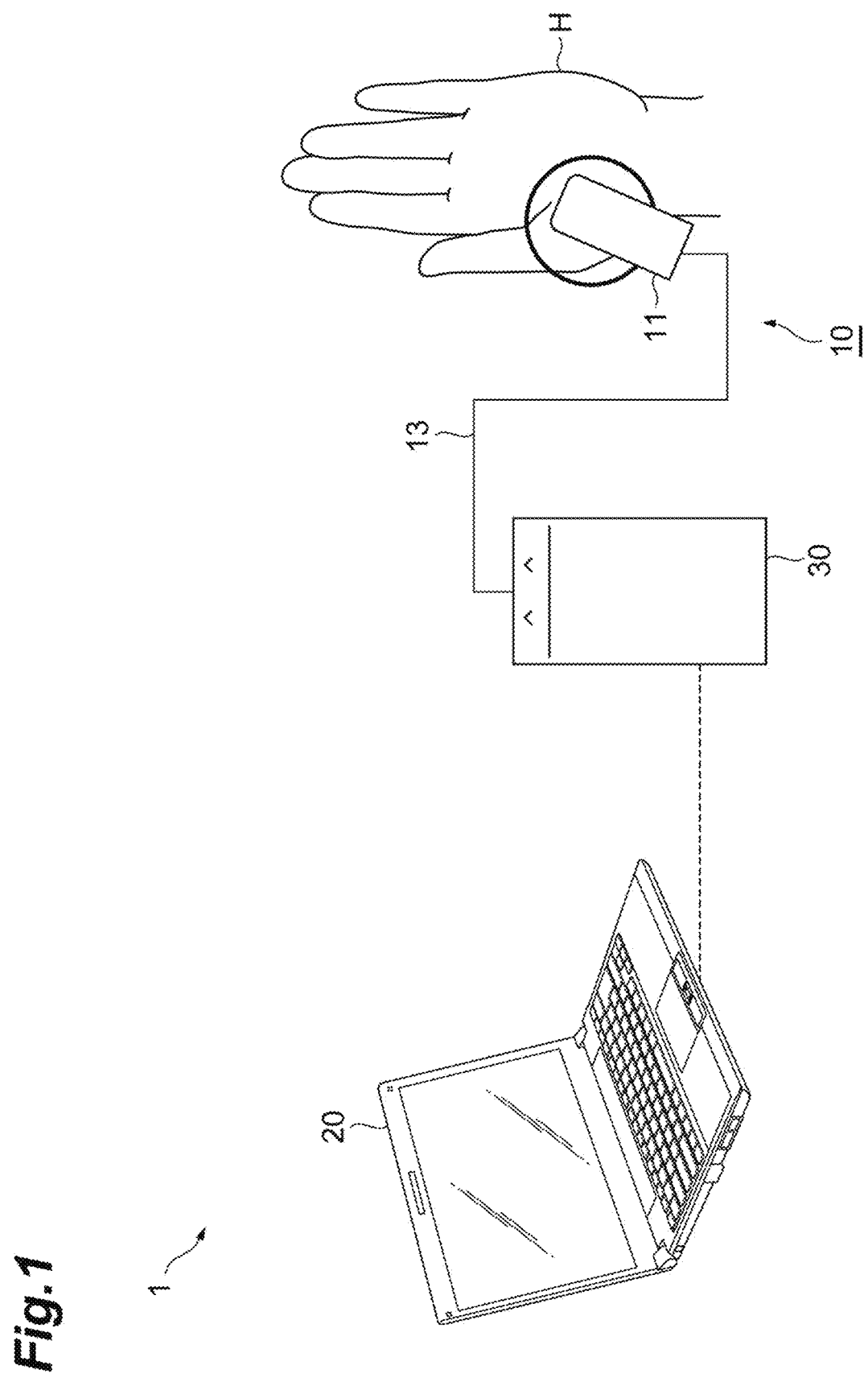
FIG. 1 is a schematic configuration diagram illustrating a blood pressure waveform estimation system including a viscoelastic characteristics acquisition device according to a first embodiment of an aspect of the present invention.

Hereinafter, embodiments of an aspect of the present invention will be described in detail with reference to the accompanying drawings. In the description, the same elements or elements having the same functions are denoted with the same reference numerals, and repeated description will be omitted.

First Embodiment

First, an overview of a blood pressure waveform estimation system including a viscoelastic characteristics acquisition device according to a first embodiment of the present invention will be described. The blood pressure waveform estimation system according to this embodiment acquires viscoelastic characteristics of a blood vessel of an inspection target (subject) and corrects a time waveform corresponding to a volume pulse wave (relative volume wave) using the acquired viscoelastic characteristics to estimate the blood pressure waveform from the time waveform corresponding to the volume pulse wave. The time waveform corresponding to the volume pulse wave is information obtained by measuring change in blood volume over time occurring at a predetermined position in the living body from a surface of the living body by irradiating the living body with light and detecting an intensity of reflected light, and taking the change as a waveform. Hereinafter, the time waveform corresponding to the volume pulse wave is simply referred to as a "volume pulse wave". The viscoelastic characteristics of the blood vessel are a viscoelasticity of the blood vessel, that is, characteristics showing a behavior of both elasticity and viscosity in the blood vessel. The blood pressure waveform is information in which temporal change in blood pressure is taken as a waveform.

The volume pulse wave is known to be influenced by viscoelastic characteristics of a blood vessel, and in order to accurately estimate a blood pressure waveform on the basis of the volume pulse wave, it is necessary to reduce the influence of the viscoelastic characteristics of the blood vessel in the volume pulse wave. Therefore, in the blood pressure waveform estimation system according to this embodiment, a viscoelastic characteristic correction value indicating the viscoelastic characteristics of the blood vessel is first acquired. By correcting the volume pulse wave using the acquired viscoelastic characteristic correction value $f_v$, a similar waveform to the blood pressure waveform in which the influence of the viscoelastic characteristics of the blood vessel has been reduced is acquired, and predetermined correction is performed on the basis of the similar waveform to the blood pressure waveform to estimate the blood pressure waveform. This will be described in detail below.

FIG. 1 is a schematic configuration diagram illustrating a blood pressure waveform estimation system including a viscoelastic characteristics acquisition device according to a first embodiment of the present invention. As illustrated in FIG. 1, the blood pressure waveform estimation system 1 includes a computer 20 and a viscoelastic characteristics acquisition device 10.

The computer 20 acquires values corresponding to a maximum blood pressure and a minimum blood pressure of an inspection target. The values corresponding to the maximum blood pressure and the minimum blood pressure of the inspection target are, for example, a maximum blood pressure value and a minimum blood pressure value, a ratio between the maximum blood pressure value and the minimum blood pressure value, or the like. The maximum blood pressure value is a systolic blood pressure value that is the highest in the systole, and the minimum blood pressure value is a diastolic blood pressure that is lowest in the diastole. In the computer 20, the maximum blood pressure value $P_{Tmax}$ and the minimum blood pressure value $P_{Tmin}$ of the inspection target measured by the blood pressure measurement device such as a cuff type sphygmomanometer or a catheter type sphygmomanometer are input by a measuring person or the like. Measurement of the maximum blood pressure value $P_{Tmax}$ and the minimum blood pressure value $P_{Tmin}$ may be performed in advance, for example, before measurement of the volume pulse wave in the viscoelastic characteristics acquisition device 10 to be described below, or may be performed at the same timing as the measurement of the volume pulse wave.

The computer 20 acquires the maximum blood pressure value $P_{Tmin}$ and the minimum blood pressure value $P_{Tmin}$ of the inspection target input by the measuring person or the like as an initial maximum blood pressure value $P_{Tmax}$ and an initial minimum blood pressure value $P_{Tmin}$ of the inspection target. The computer 20 transmits the acquired initial maximum blood pressure value $P_{Tmax}$ and the acquired initial minimum blood pressure value to the viscoelastic characteristics acquisition device 10 using wireless communication or the like. The computer 20 and the viscoelastic characteristics acquisition device 10 may be electrically connected by a cable or the like. The computer 20 may transmit the acquired initial maximum blood pressure value $P_{Tmax}$ and the acquired initial minimum blood pressure value $P_{Tmin}$ to the viscoelastic characteristics acquisition device 10 using wired communication.

The viscoelastic characteristics acquisition device 10 acquires viscoelastic characteristics of a blood vessel of the inspection target on the basis of a volume pulse wave. Specifically, the viscoelastic characteristics acquisition device 10 measures the volume pulse wave in a living body of the inspection target using, for example, so-called Near Infra-Red Spectroscopy (NIRS). The viscoelastic characteristics acquisition device 10 may include, for example, a near-infrared tissue oxygen monitoring device, a pulse oximeter, a pulse wave measurement device, or the like. The viscoelastic characteristics acquisition device 10 includes a detection unit 11 and a processing unit 30.

The detection unit 11 detects a signal for acquiring a volume pulse wave. The detection unit 11 has a form of a probe that comes into contact with a surface (in this embodiment, a palm of a hand) of a living body H that is a subject. The detection unit 11 includes a light source 11a (irradiation device) and a photodetector 11b (see FIG. 2). The detection unit 11 radiates near-infrared light from the light source 11a from the surface of the living body H to the inside thereof, and detects reflected light from the inside of the living body H using the photodetector 11b. Accordingly, the detection unit 11 acquires a absorbance when the light passes through the inside of the living body H. Since this absorbance changes according to a blood volume at a contact position of the detection unit 11 in the living body H, temporal change in this absorbance corresponds to a volume pulse wave. Examples of components that absorb light in the blood include red blood cells, hemoglobin contained in red blood cells, and moisture. The detection unit 11 is electrically connected to the processing unit 30 via a cable 13, and transmits a signal indicating the detected absorbance to the processing unit 30 via the cable 13.

The processing unit 30 acquires the volume pulse wave on the basis of the signal from the detection unit 11 and performs a predetermined process on the volume pulse wave. The processing unit 30 controls the detection unit 11. The processing unit 30 receives the signal indicating the absorbance detected by the detection unit 11, and measures the absorbance over time. Accordingly, the processing unit 30 acquires the volume pulse wave. Further, the processing unit 30 acquires an initial maximum blood pressure value $P_{Tmax}$ and an initial minimum blood pressure value $P_{Tmin}$ of the inspection target output from the computer 20 using wireless communication or the like, and a blood pressure value $P_{DN}$ at the notch point. The processing unit 30 acquires the viscoelastic characteristics of the blood vessel of the inspection target on the basis of the volume pulse wave and the initial minimum blood pressure value $P_{Tmin}$ and the initial maximum blood pressure value $T_{Tmax}$. Hereinafter, a functional configuration of the processing unit 30 will be described in detail.

Figure 2:
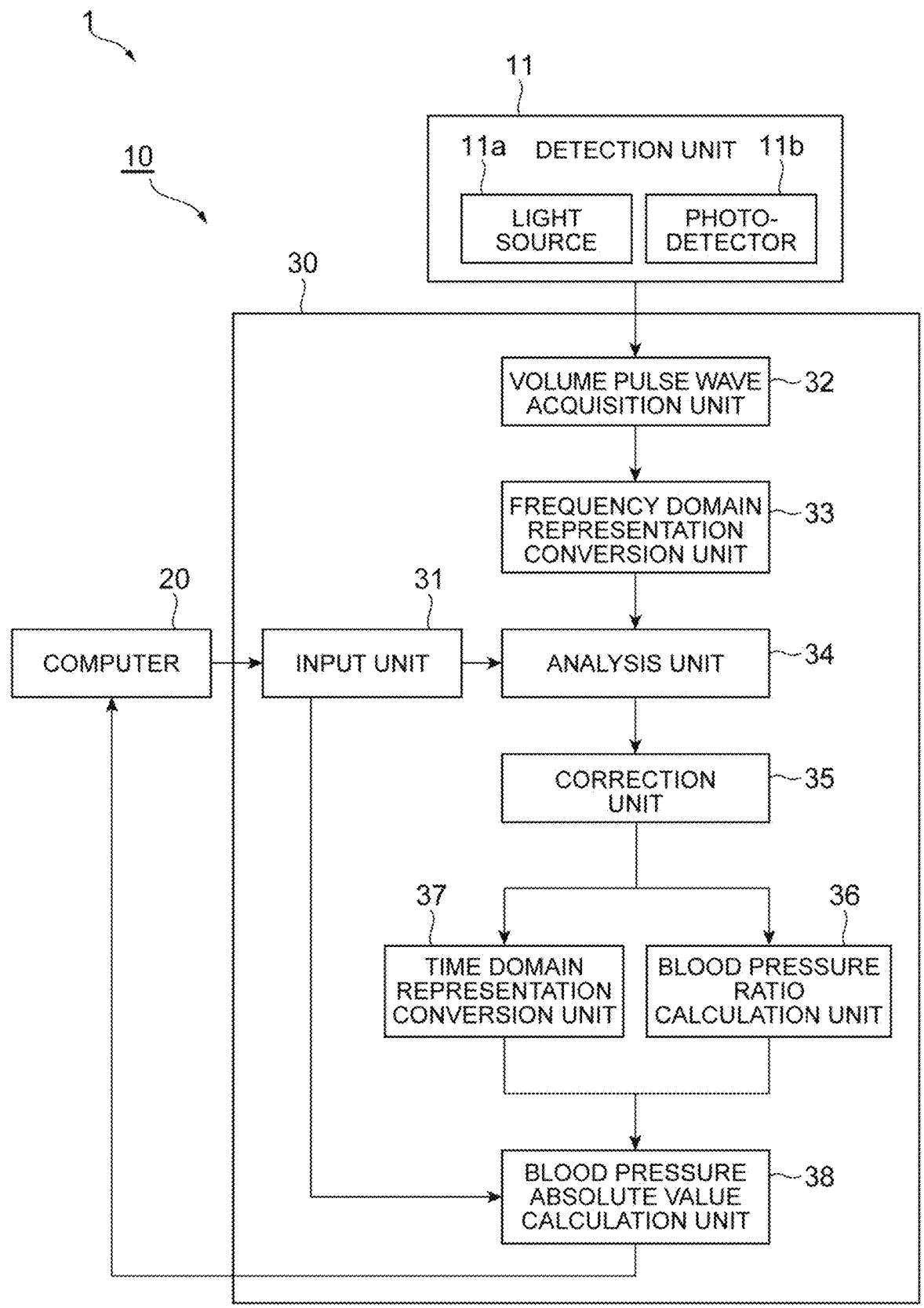
FIG. 2 is a functional block diagram of a processing unit in FIG. 1.

FIG. 2 is a functional block diagram of the processing unit 30 in FIG. 1. As illustrated FIG. 2, the processing unit 30 includes an input unit 31, a volume pulse wave acquisition unit 32, a frequency domain representation conversion unit 33 (spectrum acquisition unit), an analysis unit 34, a correction unit 35, a blood pressure ratio calculation unit 36, a time domain representation conversion unit 37, and a blood pressure absolute value calculation unit 38, which are electrically connected to each other as illustrated in FIG. 2. In this embodiment, the detection unit 11 and the volume pulse wave acquisition unit 32 function as a pulse wave acquisition unit. The blood pressure ratio calculation unit 36, the time domain representation conversion unit 37, and the blood pressure absolute value calculation unit 38 function as a blood pressure waveform acquisition unit.

The input unit 31 acquires the initial maximum blood pressure value $P_{Tmax}$ and the initial minimum blood pressure value $P_{Tmin}$ of the inspection target transmitted from the computer 20. Accordingly, the input unit 31 inputs values corresponding to the maximum blood pressure and the minimum blood pressure of the inspection target. The input unit 31 outputs the acquired initial maximum blood pressure value $P_{Tmax}$ and the acquired initial minimum blood pressure value $P_{Tmin}$ of the inspection target to the analysis unit 34 and the blood pressure absolute value calculation unit 38. The input unit 31 acquires the ratio between the initial maximum blood pressure value $P_{Tmax}$ and the initial minimum blood pressure value $P_{Tmin}$ of the inspection target transmitted from the computer 20 as values corresponding to the maximum blood pressure and the minimum blood pressure of the inspection target, and outputs the ratio to the analysis unit 34.

The volume pulse wave acquisition unit 32 receives a signal indicating the absorbance output from the detection unit 11. The volume pulse wave acquisition unit 32 acquires a volume pulse wave $LW_T$ by measuring the received absorbance over time. The volume pulse wave acquisition unit 32 outputs information on the acquired volume pulse wave $LW_T$ to the frequency domain representation conversion unit 33.

The frequency domain representation conversion unit 33 is a spectrum acquisition unit that acquires a volume pulse wave spectrum $LW_F$ by performing Fourier transform on the volume pulse wave $LW_T$ acquired by the volume pulse wave acquisition unit 32. That is, the frequency domain representation conversion unit 33 converts the volume pulse wave $LW_T$ which is a function of the time indicated in a time domain representation into a volume pulse wave spectrum $LW_F$ which is a function of the frequency indicated in a frequency domain representation. The frequency domain representation conversion unit 33 outputs information on the acquired volume pulse wave spectrum $LW_F$ to the analysis unit 34.

The analysis unit 34 acquires the viscoelastic characteristics of the blood vessel of the inspection target on the basis of the values corresponding to the maximum blood pressure and the minimum blood pressure and the volume pulse wave spectrum at a frequency equal to or higher than the frequency corresponding to the pulse of the inspection target. Specifically, the analysis unit 34 associates the initial maximum blood pressure value $P_{Tmax}$ and the initial minimum blood pressure value $P_{Tmin}$ of the inspection target acquired by the input unit 31 with information on the volume pulse wave spectrum $LW_F$ acquired by the frequency domain representation conversion unit 33 for the same inspection target. The analysis unit 34 calculates the viscoelastic characteristic correction value $f_v$ indicating the viscoelastic characteristics of the blood vessel of the inspection target using Equation (1) below on the basis of the initial maximum blood pressure value $P_{Tmax}$, the initial minimum blood pressure value $P_{Tmin}$, and the volume pulse wave spectrum $LW_F$ associated with each other for the same inspection target. Here, in Equation (1), i denotes an imaginary unit, n denotes a positive integer, $f_1$ denotes a frequency corresponding to the pulse, and $f_n$ denotes a frequency that is n times the frequency corresponding to the pulse. The analysis unit 34 outputs the calculated viscoelastic characteristic correction value f to the correction unit 35.

[Math. 1]

$$\frac{P_{T\,max}}{P_{T\,min}} = \frac{\sum_{n=1}^{N} \left|\left(1 + \frac{f_n}{f_v}i\right)LW_F(f_n)\right|}{\left|\left(1 + \frac{f_1}{f_v}i\right)LW_F(f_1)\right|} \quad (1)$$

Hereinafter, the wave at the frequency $f_1$ corresponding to the pulse in the volume pulse wave spectrum $LW_F$ is set as a first harmonic wave, and the wave at the frequency $f_n$ that is n times the frequency $f_1$ of the first harmonic wave is set as the n-th harmonic wave. The frequency $f_1$ corresponding to the pulse is in a frequency range corresponding to a pulse that a human body can take, such as about 0.5 Hz to 3.7 Hz. The frequency $f_1$ corresponding to the pulse fluctuates within the frequency range (about 0.5 Hz to 3.7 Hz) corresponding to the pulse that the human body can take due to a fluctuation of the living body, and the frequency $f_n$ also fluctuates accordingly. In Equation (1) above, $LW_F(f_1)$ indicates the spectral intensity of the first harmonic wave, and $LW_F(f_n)$ indicates the spectral intensity of the n-th harmonic wave. The spectral intensity of the first harmonic wave is, for example, the peak value of the spectral intensity of the first harmonic wave, and the spectral intensity of the n-th harmonic wave is, for example, the peak value of the spectral intensity of the n-th harmonic wave.

In a case in which the viscoelastic characteristic correction value $f_v$ is calculated using Equation (1) above, the analysis unit 34 may set N=3, for example. That is, the peak value of the spectral intensity of at least the first harmonic wave to the third harmonic wave may be used. Further, the analysis unit 34 may set N=6. That is, the peak value of the spectral intensity of the first harmonic wave to the sixth harmonic wave may be used. Further, more specifically, since a component at a frequency higher than 30 Hz in the volume pulse wave spectrum is noise, a peak value of the spectral intensity of 30 Hz or lower may be used so that such noise is not reflected in the calculation result and, preferably, a peak value of the spectral intensity of 20 Hz or lower may be used.

The above Equation (1) is derived on the basis of the following equations (2) and (3).

[Math. 2]

$$P_{T\,min}:P_{T\,max} = |P'_F(f_1)|:\sum_{n=1}^{N}|P'_F(f_n)| \quad (2)$$

[Math. 3]

$$P'_F(f) = \alpha\left(1 + \frac{f}{f_v}i\right)LW_F(f) \quad (3)$$

Equation (2) indicates a statistically significant correspondence relationship that has been newly found as a result of repeated intensive research of the present inventors. The correspondence relationship and Equation (2) will be described below in detail. Further, Equation (3) above is a model equation of a cardiovascular system based on the finding that the volume pulse wave and the blood pressure waveform are associated on the basis of the viscoelastic characteristics of the blood vessel. Equation (3) shows the volume pulse wave spectrum $LW_F$ blunted due to the influence of the viscoelastic characteristics of the blood vessel is corrected with a predetermined coefficient using the viscoelastic characteristic correction value $f_v$ showing the viscoelastic characteristics of the blood vessel, and converted into a similar blood pressure waveform spectrum $P'_F$. The similar blood pressure waveform spectrum $P'_F$ shows frequency information of a waveform similar to the blood pressure waveform. In Equation (3), α is a predetermined constant, such as 1. A model equation of the cardiovascular system shown on the basis of the finding that the volume pulse wave and the blood pressure waveform are associated on the basis of the viscoelastic characteristics may be a series spring damper model as illustrated in a part (a) of FIG. 20 or may be a series and parallel hybrid model as illustrated in a part (b) of FIG. 20.

The correction unit 35 corrects the volume pulse wave spectrum $IN_F$ acquired by the frequency domain representation conversion unit 33 using the viscoelastic characteristic correction value $f_v$ calculated by the analysis unit 34. Specifically, the correction unit 35 acquires a similar blood pressure waveform spectrum $P'_F$ by correcting the volume pulse wave spectrum $LW_F$ using the viscoelastic characteristic correction value $f_v$ and Equation (3). The correction unit 35 outputs information on the acquired similar blood pressure waveform spectrum $P'_F$ to the blood pressure ratio calculation unit 36 and the time domain representation conversion unit 37.

Figure 3:
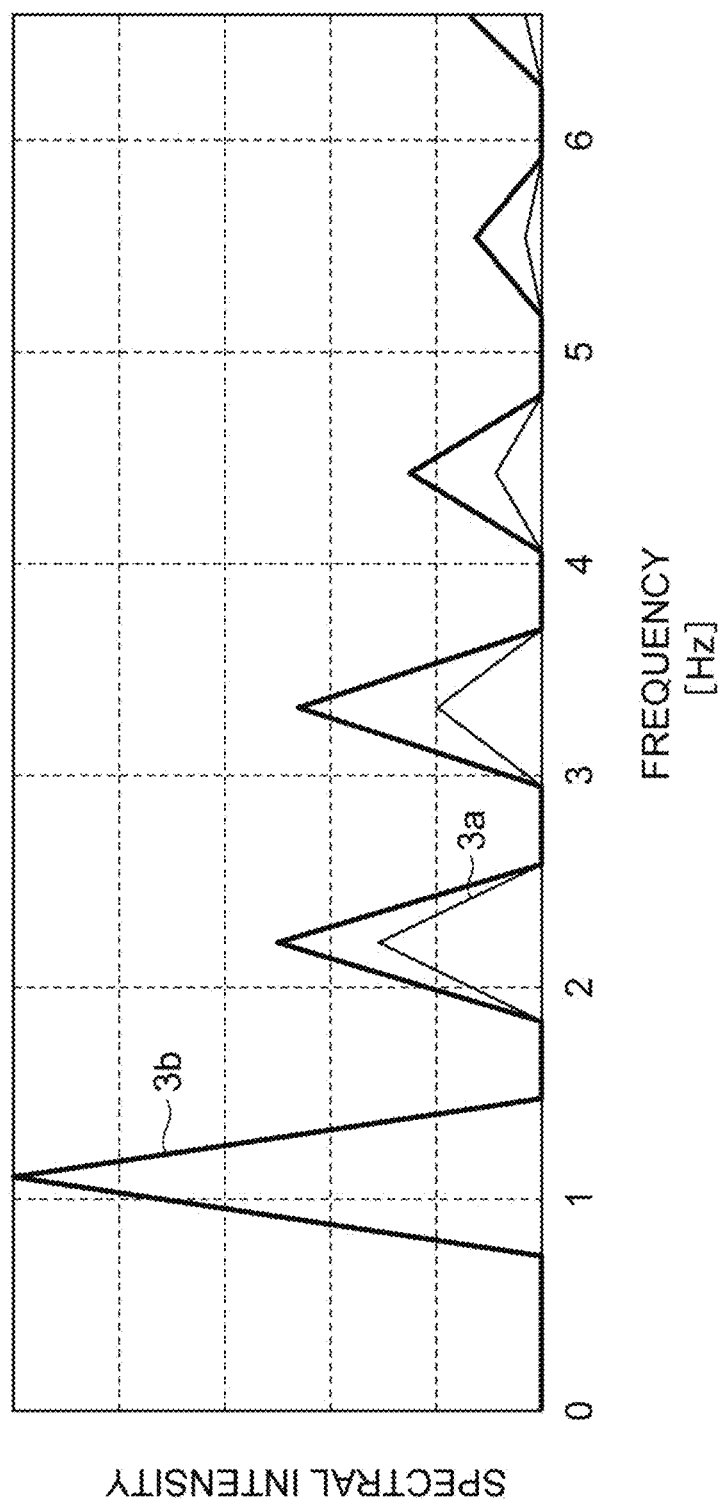
FIG. 3 is an intensity distribution diagram of a volume pulse wave spectrum and a similar blood pressure waveform spectrum.

FIG. 3 illustrates respective intensity distributions of the volume pulse wave spectrum $LW_F$ and the similar blood pressure waveform spectrum $P'_F$. A horizontal axis in FIG. 3 indicates a frequency [Hz], and a vertical axis of FIG. 3 indicates the spectral intensity. In FIG. 3, a graph 3a illustrates an intensity distribution of the volume pulse wave spectrum $LW_F$ before correction in the correction unit 35, and a graph 3b illustrates an intensity distribution of the similar blood pressure waveform spectrum $P'_F$ after correction of the correction unit 35. The intensity distributions indicated by the graphs 3a and 3b include a first harmonic wave which is a wave at a frequency $f_1$ corresponding to the pulse, and a plurality of n-th harmonics that are integer multiples thereof. In FIG. 3, since a part of the graph 3a overlaps the graph 3b, this part is not visible. For example, since the first harmonic wave of the graph 3a overlaps the first harmonic wave of the graph 3b, the first harmonic wave of the graph 3a is not visible. As illustrated in FIG. 3, the graph 3a showing the intensity distribution of the volume pulse wave spectrum $LW_F$ before correction including a blunt waveform due to the influence of the viscoelasticity of the blood vessel is corrected to the graph 3b showing the intensity distribution of the similar blood pressure waveform spectrum $P'_F$ by reducing the influence of the viscoelasticity of the blood vessel through correction of the correction unit 35.

The blood pressure ratio calculation unit 36 calculates the ratio of the maximum blood pressure value $P_{Tmax}$ to the minimum blood pressure value $P_{Tmin}$ on the basis of the similar blood pressure waveform spectrum $P'_F$ calculated by the correction unit 35. Specifically, the blood pressure ratio calculation unit 36 calculates the ratio of the maximum blood pressure value $P_{Tmax}$ to the minimum blood pressure value $P_{Tmin}$ using Equation (2) above on the basis of the similar blood pressure waveform spectrum $P'_F$. That is, the blood pressure ratio calculation unit 36 calculates a ratio of a sum of the respective peak values of the spectral intensity of the first harmonic wave or a higher harmonic wave in the similar blood pressure waveform spectrum $P'_F$ to the peak value of the spectral intensity of the first harmonic wave to calculate a ratio between the maximum blood pressure value $P_{Tmax}$ and the minimum blood pressure value $P_{Tmin}$. Hereinafter, the ratio between the maximum blood pressure value $P_{Tmax}$ and the minimum blood pressure value $P_{Tmin}$ calculated by the blood pressure ratio calculation unit 36 is also simply referred to as a "maximum-minimum blood pressure ratio". The blood pressure ratio calculation unit 36 outputs the calculated maximum-minimum blood pressure ratio to the blood pressure absolute value calculation unit 38.

The time domain representation conversion unit 37 performs inverse Fourier transform on the similar blood pressure waveform spectrum $P'_F$ calculated by the correction unit 35 to calculate the similar blood pressure waveform $P'_T$. That is, the time domain representation conversion unit 37 converts the similar blood pressure waveform spectrum $P'_F$ which is a function of a frequency indicated in a frequency domain representation into a similar blood pressure waveform $P'_T$ which is a function of time indicated in a time domain representation. The time domain representation conversion unit 37 outputs the calculated similar blood pressure waveform $P'_T$ to the blood pressure absolute value calculation unit 38. The similar blood pressure waveform $P'_T$ indicates the relative pressure, has a different value from the blood pressure waveform of the absolute pressure, but has a shape similar to the shape of the blood pressure waveform. The similar blood pressure waveform is also referred to as a relative blood pressure waveform. The similar blood pressure waveform $P'_T$ has a minimum point corresponding to the diastolic blood pressure in the blood pressure waveform, a maximum point corresponding to the systolic blood pressure in the blood pressure waveform, and a point of change corresponding to a feature point in the blood pressure waveform. The feature point in the blood pressure waveform is, for example, a point of change in blood pressure caused by an aortic valve closing due to a decrease in a blood volume, that is, the above-described notch point. It can be assumed that the blood pressure value $P_{DN}$ at the notch point is a constant value for each inspection target regardless of an exercise state of the inspection target. That is, the blood pressure value $P_{DN}$ due to the notch point can be acquired and set for each inspection target in advance.

The blood pressure absolute value calculation unit 38 performs a correction process on the similar blood pressure waveform $P'_T$ on the basis of the initial maximum blood pressure value $P_{Tmax}$ and the initial minimum blood pressure value $P_{Tmin}$ of the inspection target acquired by the input unit 31 to acquire the blood pressure waveform $P_T$ of the absolute pressure. For example, an addition coefficient is added to the similar blood pressure waveform $P'_T$ or the similar blood pressure waveform $P'_T$ is multiplied by the multiplication coefficient so that the maximum point and the minimum point in the similar blood pressure waveform $P'_T$ are substantially the same as the initial maximum blood pressure value $P_{Tmax}$ and the initial minimum blood pressure value $P^{Tmin}$ of the inspection target, to acquire the blood pressure waveform $P_T$. Further, the blood pressure absolute value calculation unit 38 may acquire the blood pressure value at a feature point such as a dicrotic notch point (hereinafter referred to as "notch point") or an average blood pressure value from the acquired blood pressure waveform $P_T$, and use the blood pressure value for subsequent acquisition of the blood pressure waveform $P_T$ (the notch point is, for example, a feature point in the blood pressure waveform caused by an aortic valve closing due to a decrease in a blood volume). For example, by performing a correction process on the similar blood pressure waveform $P'_T$ on the basis of the blood pressure value at the notch point and the maximum-minimum blood pressure ratio calculated by the blood pressure ratio calculation unit 36, the blood pressure waveform $P_T$ as the absolute pressure is obtained. More specifically, the blood pressure absolute value calculation unit 38 adds an addition coefficient to the similar blood pressure waveform $P'_T$ so that the ratio of the maximum point to minimum point in the similar blood pressure waveform $P'_T$ is substantially the same as the maximum-minimum blood pressure ratio calculated by the blood pressure ratio calculation unit 36. Further, the blood pressure absolute value calculation unit 38 multiplies the similar blood pressure waveform $P'_T$ by a multiplication coefficient so that the blood pressure value at the notch point in the similar blood pressure waveform $P'_T$ is substantially the same as the blood pressure value at the notch point acquired from the blood pressure waveform $P_T$. Through such a correction process, the blood pressure absolute value calculation unit 38 acquires a subsequent blood pressure waveform $P_T$.

Figure 4:
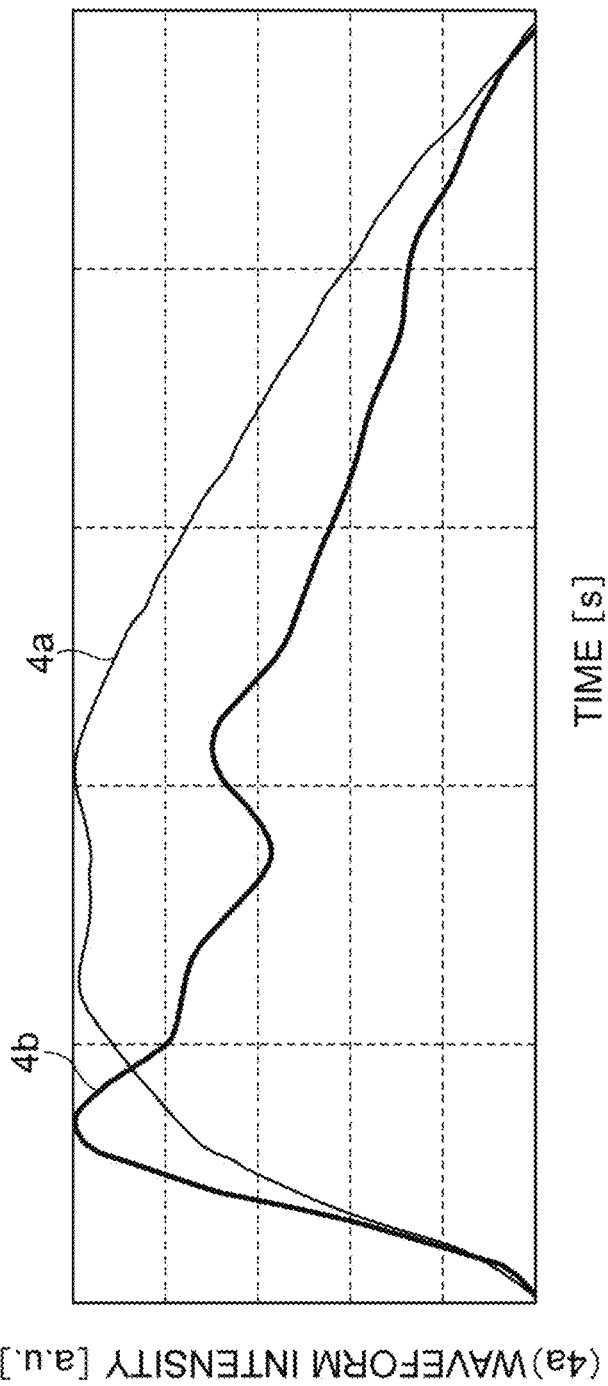
FIG. 4 is a graph showing a volume pulse wave and a blood pressure waveform.

FIG. 4 illustrates a graph of the volume pulse wave $LW_T$ and the blood pressure waveform $P_T$. A horizontal axis of FIG. 4 indicates time [s], and a vertical axis of FIG. 4 indicates waveform intensity [a. u.] and the blood pressure [mmHg]. In FIG. 4, a graph 4a shows the volume pulse wave $LW_T$ and a graph 4b shows the blood pressure waveform $P_T$. As illustrated in FIG. 4, the graph 4a showing the volume pulse wave $LW_T$ output from the volume pulse wave acquisition unit 32 is obtained as the graph 4b showing the blood pressure waveform $P_T$ by performing respective processes in the frequency domain representation conversion unit 33, the analysis unit 34, the correction unit 35, the blood pressure ratio calculation unit 36, the time domain representation conversion unit 37, and the blood pressure absolute value calculation unit 38. The blood pressure waveform $P_T$ shown in the graph 4b corresponds to a blood pressure waveform obtained by actually performing measurement on a measurement target using a sphygmomanometer or the like. That is, the blood pressure waveform is reproduced from the volume pulse wave.

The blood pressure absolute value calculation unit 38 transmits information on the acquired blood pressure waveform $P_T$ to the computer 20 using wireless communication or the like. The computer 20 includes a display unit such as a display, and displays the blood pressure waveform $P_T$ on the display on the basis of the information on the blood pressure waveform $P_T$ transmitted from the blood pressure absolute value calculation unit 38. Further, the computer 20 may display the blood pressure value on the display on the basis of the blood pressure waveform $P_T$ in real time, or may display the maximum-minimum blood pressure value, the average blood pressure value, or the like each cycle. Further, a pulse rate may be obtained by the volume pulse wave acquisition unit 32, and the pulse rate may be displayed on the display of the computer 20 at the same time as the waveform or the blood pressure value. The viscoelastic characteristics acquisition device 10 may include a display unit such as a display, and the blood pressure waveform $P_T$ or the like may be displayed by the display unit included in the viscoelastic characteristics acquisition device 10.

Figure 5:
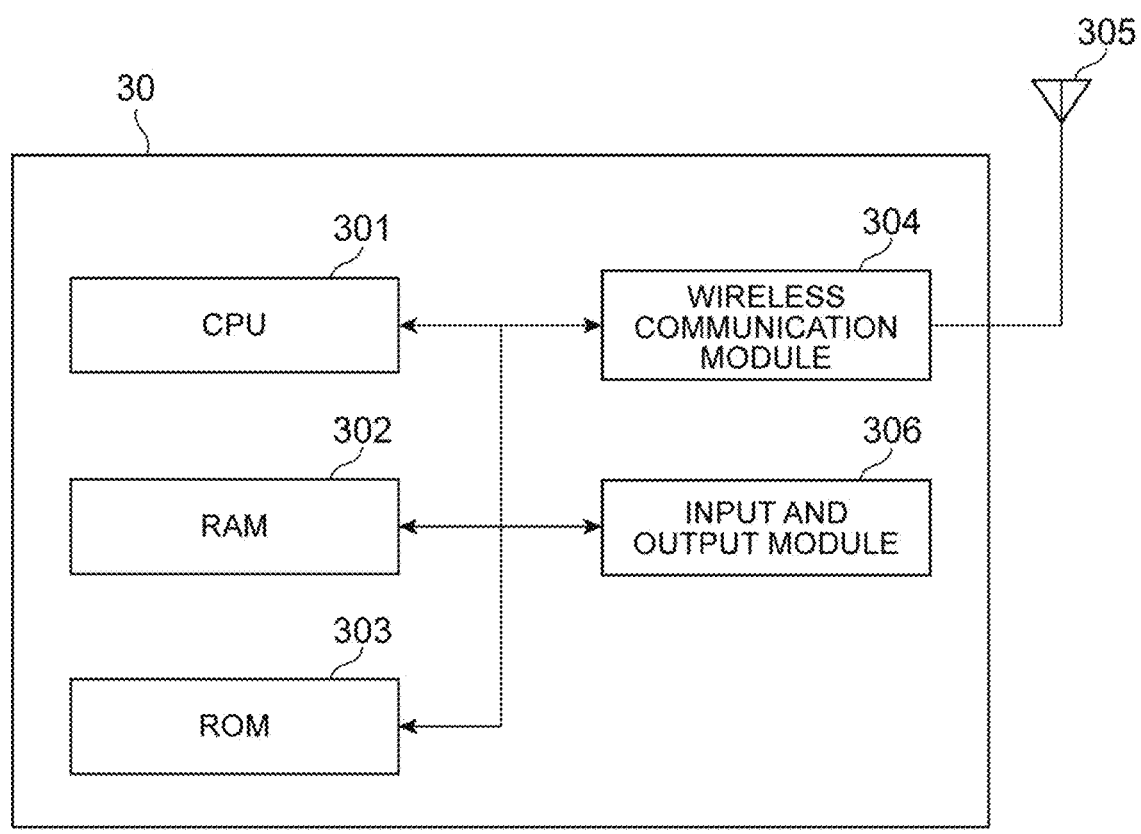
FIG. 5 is a diagram illustrating a hardware configuration of a processing unit in FIG. 1.

Next, a hardware configuration of the processing unit 30 will be described with reference to FIG. 5. FIG. 5 illustrates a hardware configuration of the processing unit 30 in FIG. 1. As illustrated in FIG. 5, the processing unit 30 physically is a computer including, for example, a central processing unit (CPU) 301 that is a processor, a random access memory (RAM) 302 or a read only memory (ROM) 303 that is a recording medium, a wireless communication module 304, an antenna 305, and an input and output module 306, which are electrically connected. Each function of the processing unit 30 described above is realized by operating, for example, the wireless communication module 304, the antenna 305, and the input and output module 306 under control of the CPU 301 by loading the viscoelastic characteristics acquisition program or the like on hardware such as the CPU 301 and the RAM 302, and performing reading and writing of data in the RAM 302. The processing unit 30 may include a display, an operation module, or the like.

Next, the correspondence relationship shown in Equation (2) above discovered by the present inventors will be described in detail.

Figure 6:
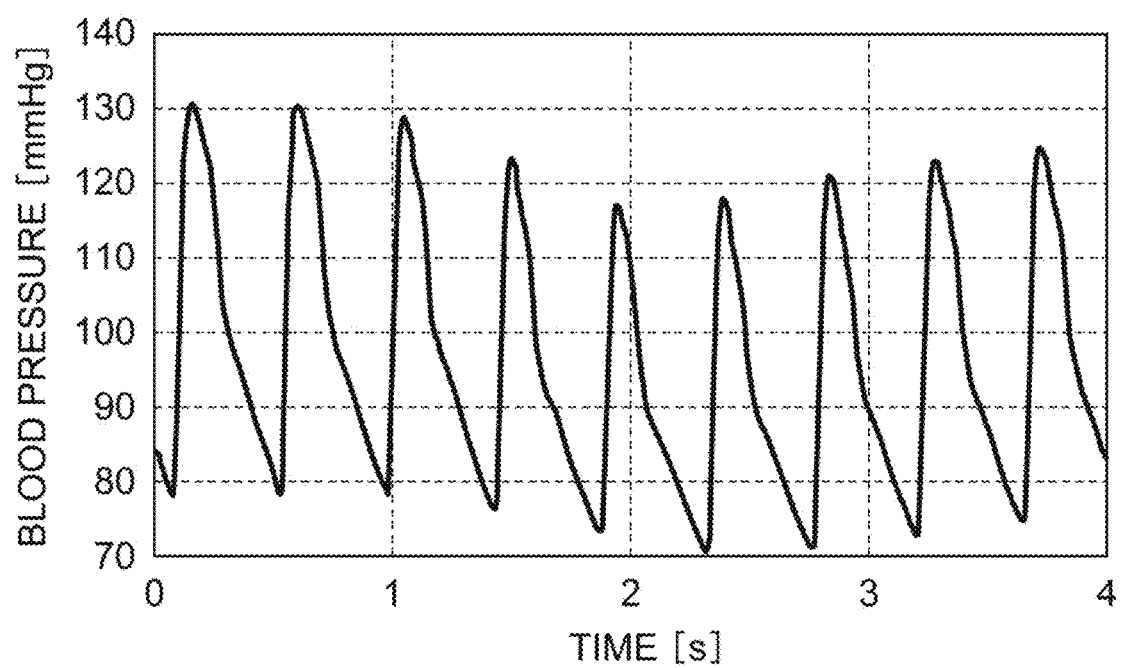
FIG. 6 is a graph showing a blood pressure waveform.
Figure 7:
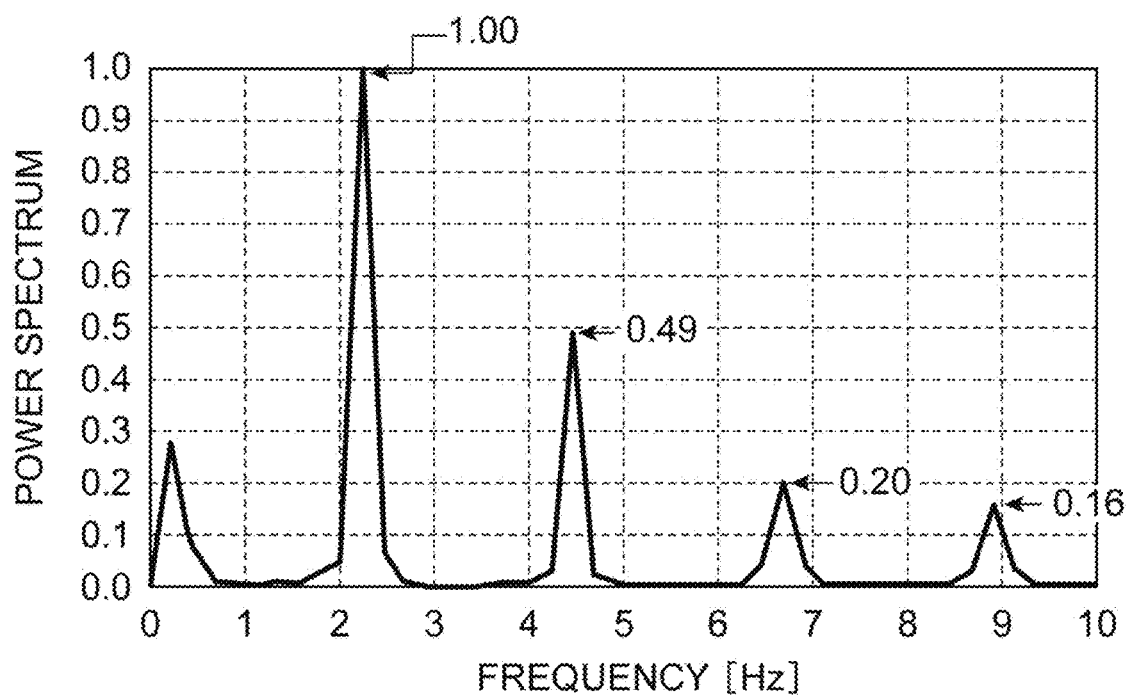
FIG. 7 is a graph showing a power spectrum of the blood pressure waveform illustrated in FIG. 6.

FIG. 6 is a graph showing a blood pressure waveform. A horizontal axis of FIG. 6 indicates time [s], and a vertical axis of FIG. 6 indicates blood pressure [mmHg]. In the graph illustrated in FIG. 6, the maximum blood pressure value $P_{Tmax}$ is about 130 mmHg and the minimum blood pressure value $P_{Tmin}$ is about 70 mmHg. Therefore, a ratio between the maximum blood pressure value $P_{Tmax}$ and the minimum blood pressure value $P_{Tmin}$, that is, the maximum-minimum blood pressure ratio is about 1.86. The blood pressure waveform mainly includes a first harmonic wave (main wave) at the frequency $f_1$ corresponding to the pulse, and an n-th harmonic wave at the frequency $f_n$ higher than the frequency $f_1$. When the blood pressure waveform illustrated in FIG. 6 is subjected to Fourier transform, a power spectrum as illustrated in FIG. 7 is obtained:

FIG. 7 is a graph showing a power spectrum obtained by performing Fourier transform on the blood pressure waveform illustrated in FIG. 6. The power spectrum is normalized using a spectral intensity of the first harmonic wave. A horizontal axis of FIG. 6 indicates a frequency [Hz], and a vertical axis of FIG. 7 indicates the spectral intensity. As a result of intensive research, the present inventors have found that in the power spectrum illustrated in FIG. 7, a ratio of the sum of the spectral intensities of the n-th harmonic wave that is equal to or higher than the first harmonic wave to the intensity of the spectrum of the first harmonic wave (hereinafter referred to as a "ratio based on a spectral intensity") is substantially equal to the maximum-minimum blood pressure ratio obtained from the blood pressure waveform illustrated in FIG. 6. Specifically, in the power spectrum illustrated in FIG. 7, a sum of the spectral intensities of the n-th harmonic wave equal to or higher than the first harmonic wave is 1.00+0.49+0.20+0.16=1.85. Therefore, the ratio of the sum of the spectral intensities of the n-times harmonic wave equal to or higher than the first harmonic wave to the spectral intensity of the first harmonic wave is 1.85 and is substantially equal to about 1.86 that is the ratio of the maximum blood pressure value $P_{Tmax}$ and the minimum blood pressure value $P_{Tmin}$. This correspondence relationship can be expressed by Equation (2) above.

Figure 8:
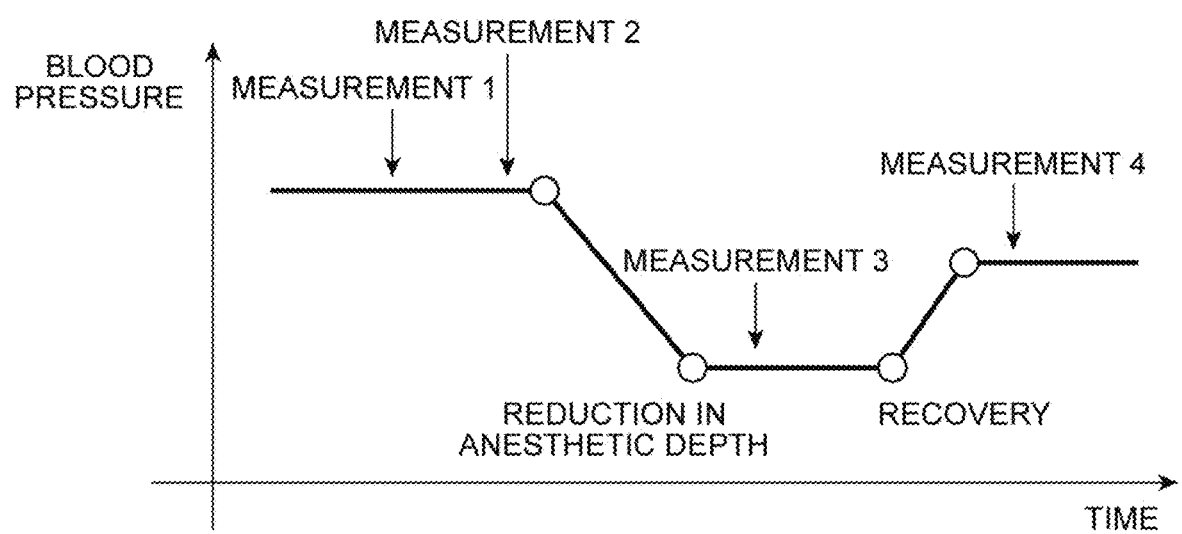
FIG. 8 is a graph showing a fluctuation in blood pressure of a cynomolgus monkey due to an anesthetic agent.

The present inventors have confirmed that the correspondence relationship shown in Equation (2) above is statistically significant from the following experiment. The present inventors have continuously measured a blood pressure waveform indicating a fluctuation in blood pressure of a cynomolgus monkey while applying an isoflurane anesthetic agent having different concentrations to the cynomolgus monkey and causing the blood pressure to fluctuate in a state in which an invasive sphygmomanometer is installed in an artery of a foot of the cynomolgus monkey. FIG. 8 illustrates a fluctuation in blood pressure of the cynomolgus monkey due to the anesthetic agent. In FIG. 8, a horizontal axis indicates time and a vertical axis of FIG. 8 indicates blood pressure.

Figure 9:
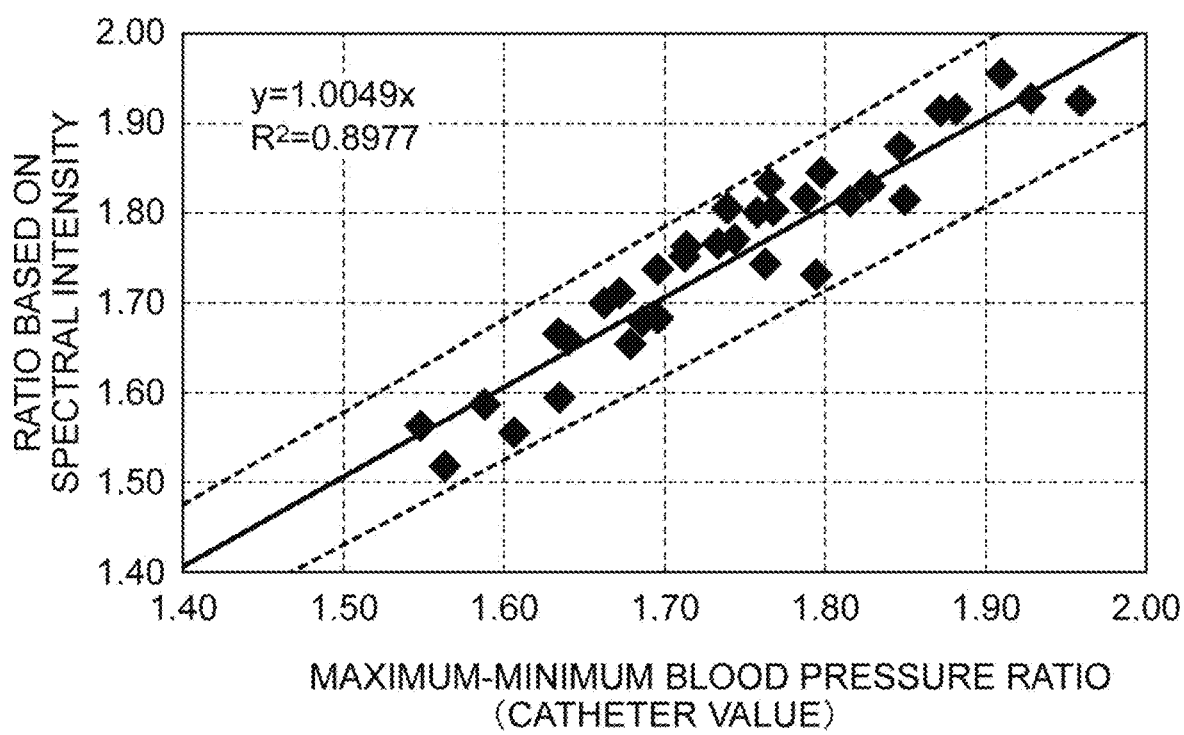
FIG. 9 is a graph showing a correlation between a ratio between a maximum blood pressure and a minimum blood pressure and a ratio based on a spectral intensity of the blood pressure waveform.

A plurality of pieces of data in different time periods in the measured blood pressure waveform are extracted, and a relationship between the ratio between the maximum blood pressure and the minimum blood pressure obtained from the extracted data and the ratio based on the spectral intensity obtained by performing Fourier transform on the blood pressure waveform has been plotted as illustrated in a graph of FIG. 9, and a correlation thereof has been confirmed. A horizontal axis of FIG. 9 indicates the maximum-minimum blood pressure ratio obtained by an experiment performed on the cynomolgus monkey, and a vertical axis of FIG. 9 indicates the ratio based on the spectral intensity obtained by performing Fourier transform on the blood pressure waveform. As illustrated in FIG. 9, the ratio based on the spectral intensity obtained by performing Fourier transform on the blood pressure waveform has been confirmed to fall within a range of ±5% of the ratio between the maximum blood pressure and the minimum blood pressure obtained by the experiment performed on the cynomolgus monkey.

The above shows that the correspondence relationship shown in Equation (2) above is statistically significant. On the basis of Equation (2) and Equation (3) above which is a model equation of the viscoelastic characteristics, Equation (1) above is derived.

The precision of the relationship shown in Equation (2) above depends on frequency resolution of the Fourier transform. When one pulse wave is considered, ideally, there are no waves other than an integer multiple harmonic wave of a frequency corresponding to the pulse. However, when a plurality of pulse waves are considered, waves other than an integer multiple harmonic wave of the frequency corresponding to the pulse are included due to biological fluctuations.

In principle, the frequency resolution due to the Fourier transform depends on a length of a time waveform before the transform, but since an actually measured time waveform has a finite length, a spectrum of the time waveform cannot be completely separated for each frequency. The spectrum of each integer multiple harmonic wave includes a spectrum of a peripheral wave other than an integer multiple harmonic wave. As the frequency resolution is higher, waves other than an integer multiple harmonic wave can be removed, and the accuracy of the relationship shown in Equation (2) above is improved. Conversely, as the frequency resolution is lower, the accuracy is degraded under an influence of the waves other than the integer multiple harmonic wave. Although there is a difference in accuracy according to the frequency resolution of the Fourier transform, the correspondence relationship shown in Equation (2) above is kept statistically significant.

Figure 10:
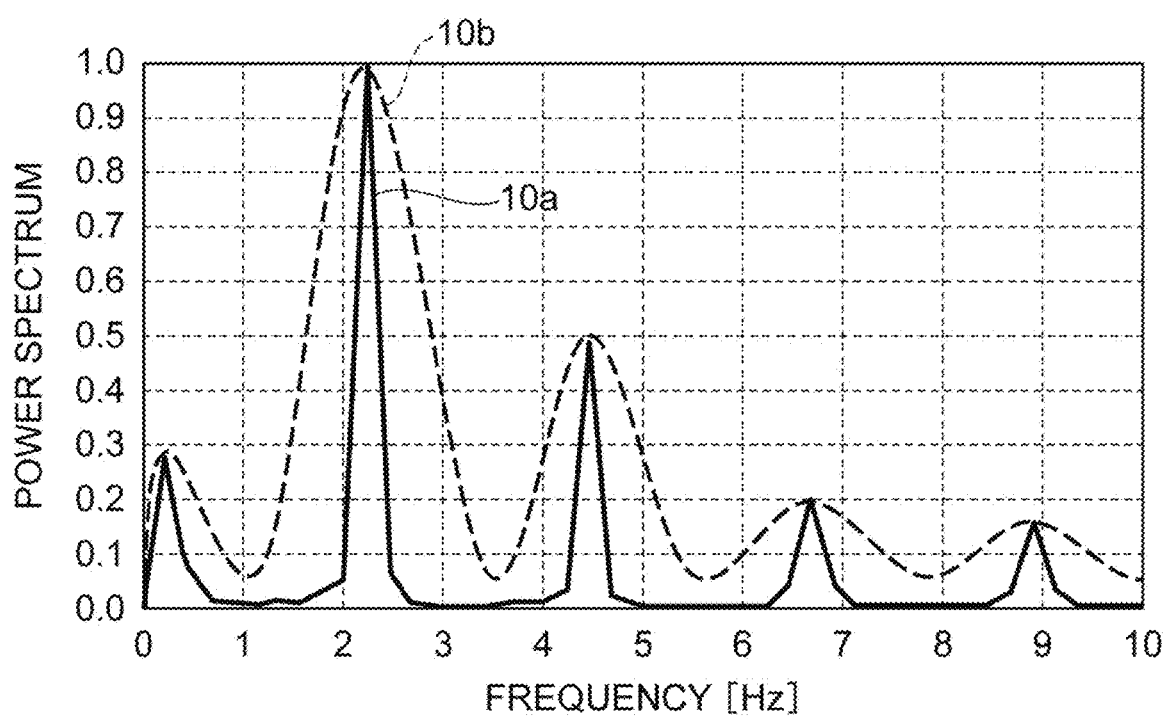
FIG. 10 is a graph showing a spread of a power spectrum of a blood pressure waveform due to biological fluctuations.

FIG. 10 is a graph showing spread of a power spectrum of the blood pressure waveform due to biological fluctuations. A horizontal axis of FIG. 10 indicates a frequency [Hz], and a vertical axis of FIG. 10 indicates the spectral intensity. A graph 10a in FIG. 10 shows a power spectrum of an ideal blood pressure waveform in which the biological fluctuation is ignored, and a graph 10b in FIG. 10 shows a power spectrum of a blood pressure waveform including waves other than an integer multiple harmonic wave due to biological fluctuations. The graph 10b showing the power spectrum of the blood pressure waveform including waves other than the integer multiple harmonic wave due to the biological fluctuation has a wider mountain of each peak than the graph 10a showing the power spectrum of the ideal blood pressure waveform in which the biological fluctuation is ignored.

The present inventors have found that in the power spectrum of the blood pressure waveform including waves other than integer multiple harmonic waves due to biological fluctuations in this manner, the ratio of the sum of the spectral intensities of the n-th harmonic wave group equal to or higher than the first harmonic wave group to the spectral intensity of the first harmonic wave group is substantially equal to the ratio between the maximum blood pressure value $P_{Tmax}$ and the minimum blood pressure value $P_{Tmin}$. That is, the inventors have found that the correspondence relationship expressed by Equation (4) below is satisfied. That is, the present inventors have found that the correspondence relationship shown in Equation (4) below is satisfied. The first harmonic wave group is a group of waves at a frequency in a predetermined range of the frequency $f_1$ corresponding to the pulse, including the frequency $f_1$ corresponding to the pulse. More specifically, the first harmonic wave group is, for example, a spectrum in a range with a predetermined effective width around a peak value of a spectral intensity of the first harmonic wave. The spectral intensity of the first harmonic wave group is, for example, an integral value of the spectral intensity in a predetermined effective width. An n-th harmonic wave group is a group of waves at a frequency in a predetermined width of a frequency $f_n$, including the frequency $f_n$ which is n times the frequency $f_1$ corresponding to the pulse. More specifically, the n-th harmonic wave group is, for example, a spectrum in a range with a predetermined effective width around a peak value of the spectral intensity of the n-th harmonic wave. The spectral intensity of the n-th harmonic wave group is, for example, an integral value of the spectral intensity in a predetermined effective width.

[Math. 4]

$$P_{T\,min} : P_{T\,max} = \int_{-d}^{d}\left|P'_F\left(f_1 + \frac{f}{2}\right)\right|df : \sum_{n=1}^{N}\int_{-d}^{d}\left|P'_F\left(f_n + \frac{f}{2}\right)\right|df \quad (4)$$

The predetermined effective width may be, for example, a frequency width W1 which corresponds to a half value of the peak value of the spectral intensity of the n-th harmonic wave as illustrated in FIG. 11(a) or may be, for example, a frequency width W2 separated at a center between frequencies of the adjacent n-th harmonic waves as illustrated in FIG. 11(b). An optimum frequency resolution or the effective width of the spectrum group may be appropriately set in consideration of device characteristics of the viscoelastic characteristics acquisition device, biological fluctuations, or the like.

The analysis unit 34 may acquire the viscoelastic characteristics on the basis of Equation (4) and Equation (3) that is a model equation of the viscoelastic characteristics instead of Equation (1) above. That is, the analysis unit 34 may calculate the viscoelastic characteristic correction value $f_v$ on the basis of the maximum-minimum blood pressure ratio and the sum of the intensities of the respective volume pulse wave spectra of the first harmonic wave group or a higher harmonic wave group. In this case, in Equation (4) above, the analysis unit 34 may set N=3. That is, the integral value of the spectral intensity of at least the first harmonic wave group to the third harmonic wave group may be used. Further, the analysis unit 34 may set N=6. That is, the integral value of the spectral intensity from the first harmonic wave group to the sixth harmonic wave group may be used. Further, more specifically, since a component at a frequency higher than 30 Hz in the volume pulse wave spectrum is noise, an integral value of a spectral intensity of 30 Hz or less may be used such that noise is not reflected in a calculation result and, preferably, an integral value of a spectral intensity of 20 Hz or less may be used.

Figure 12:
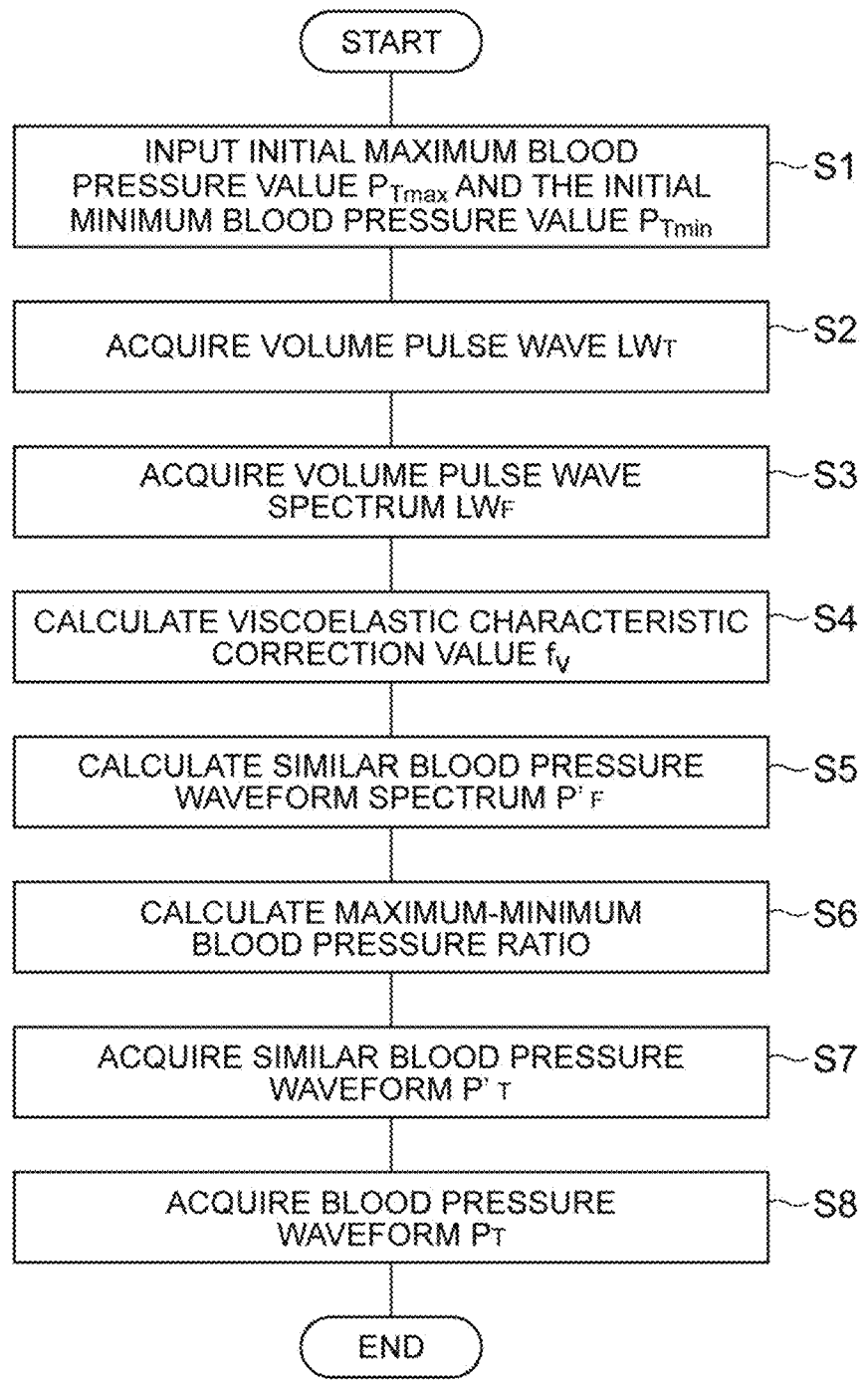
FIG. 12 is a flow diagram illustrating a processing procedure in the blood pressure waveform estimation system.

Next, a processing procedure of acquiring the viscoelastic characteristics of the blood vessel using the blood pressure waveform estimation system 1 including the viscoelastic characteristics acquisition device 10 according to this embodiment, and estimating the blood pressure waveform on the basis of the viscoelastic characteristics will be described with reference to the flowchart of FIG. 12. FIG. 12 is a flow diagram illustrating a processing procedure in the blood pressure waveform estimation system 1.

As a premise of this process, the initial maximum blood pressure value $P_{Tmax}$ and the initial minimum blood pressure value $P_{Tmin}$ of the inspection target are recorded in the computer 20 in advance. When the connection using wireless communication is established between the computer 20 and the processing unit 30 of the viscoelastic characteristics acquisition device 10, the initial maximum blood pressure value $P_{Tmax}$ and the initial minimum blood pressure value $P_{Tmin}$ are transmitted from the computer 20 to the input unit 31. Accordingly, the initial maximum blood pressure value $P_{Tmax}$ and the initial minimum blood pressure value $P_{Tmin}$ are input to the input unit 31 (S1: input step).

Subsequently, the volume pulse wave acquisition unit 32 acquires the volume pulse wave $LW_T$ on the basis of the signal from the detection unit 11 (S2: volume pulse wave acquisition step). Subsequently, the frequency domain representation conversion unit 33 performs Fourier transform on the volume pulse wave $LW_T$ acquired in S2 to acquire the volume pulse wave spectrum $LW_F$ (S3: spectrum acquisition step). Subsequently, the analysis unit 34 calculates the viscoelastic characteristic correction value $f_v$ indicating the viscoelastic characteristics of the blood vessel on the basis of the volume pulse wave spectrum $LW_F$ acquired in S3 (S4: analysis step). Through the processes of S1 to S4, the viscoelastic characteristics of the blood vessel are acquired. In subsequent S5 to S8, a process of estimating the blood pressure waveform is performed on the basis of the acquired viscoelastic characteristic correction value $f_v$.

On the basis of the volume pulse wave spectrum $LW_F$ calculated in S3 and the viscoelastic characteristic correction value $f_v$ calculated in S4, the correction unit 35 corrects the volume pulse wave spectrum using Equation (3) above and calculates the similar blood pressure waveform spectrum $P'_F$ (S5: correction step). Further, the blood pressure ratio calculation unit 36 calculates the maximum-minimum blood pressure ratio using Equation (2) above on the basis of the similar blood pressure waveform spectrum $P'_F$ calculated in S5 (S6: blood pressure waveform acquisition step). Subsequently, the time domain representation conversion unit 37 performs inverse Fourier transform on the similar blood pressure waveform spectrum $P'_F$ calculated in S5 to acquire the similar blood pressure waveform $P'_T$ (S7: blood pressure waveform acquisition step). Subsequently, the blood pressure absolute value calculation unit 38 adds an addition coefficient to the similar blood pressure waveform $P'_T$ or multiplies the similar blood pressure waveform $P'_T$ by the multiplication coefficient so that the maximum point and the minimum point in the similar blood pressure waveform $P'_T$ are substantially the same as the initial maximum blood pressure value $P_{Tmax}$ and the initial minimum blood pressure value $P_{Tmin}$ of the inspection target, to acquire the blood pressure waveform $P_T$. Further, the blood pressure absolute value calculation unit 38 acquires, for example, the blood pressure value $P_{DN}$ at the notch point as the feature point from the acquired blood pressure waveform $P_T$, and thereafter, and performs a correction process on the similar blood pressure waveform $P'_T$ on the basis of the maximum-minimum blood pressure ratio calculated in S6 and the blood pressure value $P_{DN}$ at the notch point, to acquire the blood pressure waveform $P_T$ (S8: blood pressure waveform acquisition step). In steps S5 to S8 above, the blood pressure waveform is estimated and the process is ended. The information indicating the blood pressure waveform $P_T$ acquired in S8 may be displayed on, for example, the display of the computer 20 by being transmitted from the processing unit 30 to the computer 20.

Figure 13:
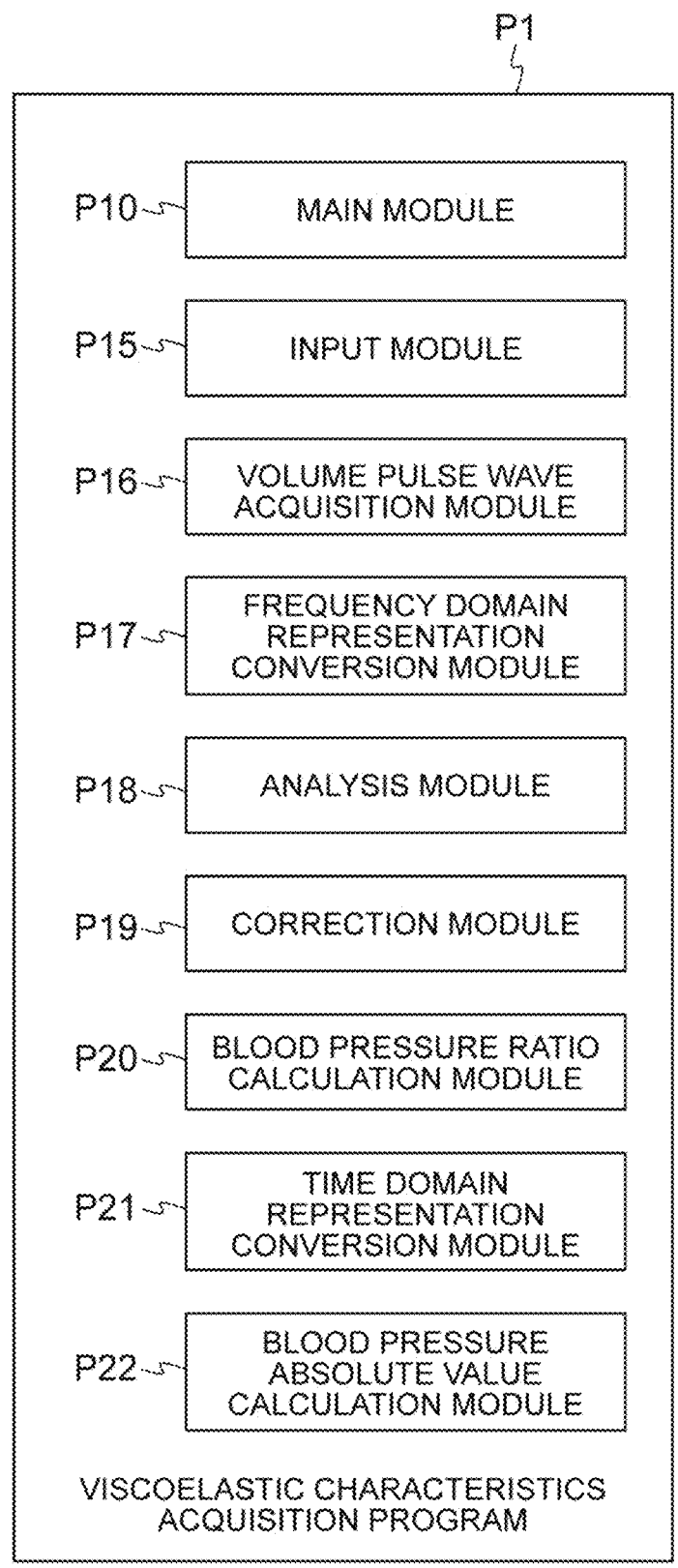
FIG. 13 is a diagram illustrating a configuration of a viscoelastic characteristics acquisition program according to an embodiment of an aspect of the present invention.

Next, the viscoelastic characteristics acquisition program for causing a computer to function as the viscoelastic characteristics acquisition device 10 will be described with reference to FIG. 13.

The viscoelastic characteristics acquisition program P1 includes a main module P10, an input module P15, a volume pulse wave acquisition module P16, a frequency domain representation conversion module P17, an analysis module P18, a correction module P19, a blood pressure ratio calculation module P20, a time domain representation conversion module P21, and a blood pressure absolute value calculation module P22.

The main module P10 is a part that totally controls the entire viscoelastic characteristics acquisition process. Functions realized by executing the input module P15, the volume pulse wave acquisition module P16, the frequency domain representation conversion module P17, the analysis module P18, the correction module P19, the blood pressure ratio calculation module P20, the time domain representation conversion module P21, and the blood pressure absolute value calculation module P22 are the same as those of the input unit 31, the volume pulse wave acquisition unit 32, the frequency domain representation conversion unit 33, the analysis unit 34, the correction unit 35, the blood pressure ratio calculation unit 36, the time domain representation conversion unit 37, and the blood pressure absolute value calculation unit 38 of the viscoelastic characteristics acquisition device 10, respectively.

The viscoelastic characteristics acquisition program P1 is provided by, for example, a recording medium or a semiconductor memory such as a CD-ROM, a DVD, or a ROM. Further, the viscoelastic characteristics acquisition program P1 may be provided over a network as a computer data signal superimposed on a carrier wave.

As described above, according to the viscoelastic characteristics acquisition device 10, the viscoelastic characteristics acquisition method, the viscoelastic characteristics acquisition program, and the recording medium having the program recorded thereon according to this embodiment, the viscoelastic characteristic correction value $f_v$ indicating the viscoelastic characteristics is acquired on the basis of the maximum blood pressure value $P_{Tmax}$ and the minimum blood pressure value $P_{Tmin}$ of the inspection target and the volume pulse wave spectrum $LW_F$ at the frequency $f_1$ or higher corresponding to the pulse of the inspection target. Accordingly, it possible to conveniently acquire highly accurate viscoelastic characteristics. It is possible to evaluate the cardiovascular system on the basis of the viscoelastic characteristics.

More specifically, in the viscoelastic characteristics acquisition device 10 according to the above embodiment, the analysis unit 34 can acquire the viscoelastic characteristic correction value $f_v$ sufficiently and accurately on the basis of the maximum blood pressure value $P_{Tmax}$, the minimum blood pressure value $P_{Tmin}$ of the inspection target, and a sum of the intensities of the volume pulse wave spectra including the intensities of the volume pulse wave spectra LW$_F$ of at least the first harmonic wave to the third harmonic wave of the inspection target.

Further, even when the spectral intensity of each nth harmonic wave spreads in a Gaussian shape in the frequency direction due to the influence of the biological fluctuation, the respective spread spectrum intensities are set as the spectral intensities of the n-th harmonic wave group, and it is possible to acquire the viscoelastic characteristic correction value f$_v$ sufficiently and accurately on the basis of the maximum blood pressure value P$_{Tmax}$ and the minimum blood pressure value P$_{Tmin}$ of the inspection target, and the sum of the intensities of the volume pulse wave spectrum including the intensities of the respective volume pulse wave spectra of at least the first harmonic wave group to the third harmonic wave group of the inspection target.

Further, according to this embodiment, the volume pulse wave LW$_T$ is corrected on the basis of the viscoelastic characteristic correction value f$_v$ indicating the relationship between the volume pulse wave LW$_T$ and the blood pressure waveform P$_T$, and the blood pressure waveform P$_T$ is acquired on the basis of the corrected volume pulse wave LW$_T$. Thus, the blood pressure waveform P$_T$ can be accurately estimated from the volume pulse wave LW$_T$, and the cardiovascular system can be evaluated on the basis of the estimated blood pressure waveform conveniently, sufficiently, and accurately.

Further, according to this embodiment, by detecting the light radiated from the light source 11a included in the detection unit 11 and transmitted through the inside of the living body using the photodetector 11b included in the detection unit 11, it is possible to easily acquire the volume pulse wave LW$_T$ without providing a device that detects a signal for acquiring the volume pulse wave LW$_T$ separately from the viscoelastic characteristics acquisition device 10.

Second Embodiment

Next, an overview of a blood vessel age estimation system including a viscoelastic characteristics acquisition device according to a second embodiment will be described. The blood vessel age estimation system according to this embodiment is a system that acquires viscoelastic characteristics of a blood vessel of an inspection target (subject) and estimates a blood vessel age of the measurement target using the acquired viscoelastic characteristics. The blood vessel age refers to an age of a blood vessel, and is an indicator showing how much the blood vessel has aged through a comparison with an actual age. A human blood vessel is known to gradually lose flexibility and become hard and brittle with age. Such an aging phenomenon of a blood vessel is generally called arteriosclerosis and causes stroke, angina pectoris, myocardial infarction, or the like, and therefore, the existence of a device that routinely and conveniently measures a degree of progression of arteriosclerosis is very useful.

In general, a scheme of using a stiffness parameter β (hereinafter also referred to as "stiffness β") is widely known as an indicator of the degree of progression of arteriosclerosis. The stiffness β is calculated on the basis of Equation (5) below by echocardiography, CAVI examination using pulse wave propagation velocity, or the like. Here, p$_S$ and p$_d$ are the maximum blood pressure and the minimum blood pressure at the measurement part, d is a diameter of the blood vessel at the measurement part, and Δd is an amount of change in diameter of the blood vessel due to pulsation. By comparing the value of this stiffness β with, for example, an average value for a human of the same age, the blood vessel age of the subject can be obtained.

[Math. 5]

$$\beta = \ln\left(\frac{p_s}{p_d}\right) \cdot \frac{d}{\Delta d} \quad (5)$$

In Equation (5) for obtaining the stiffness β, it is generally difficult to calculate the amount of change in diameter Δd of the blood vessel. In the current technology, the stiffness β is obtained, for example, by measuring d and Δd using a large-scale device for echocardiography or the like or indirectly calculating Δd/d using the pulse wave propagation velocity. Further, it is preferable to originally measure, record and manage the stiffness β with a short period of such as one month to daily, rather than a long period such as once a year, but an opportunity to receive a current CAVI examination is limited.

Therefore, in the blood vessel age estimation system according to this embodiment, first, a viscoelastic characteristic correction value f$_v$ indicating the viscoelastic characteristics of a blood vessel is acquired. The blood vessel age is estimated on the basis of the acquired viscoelastic characteristic correction value f$_v$. This will be described in detail below.

Figure 14:
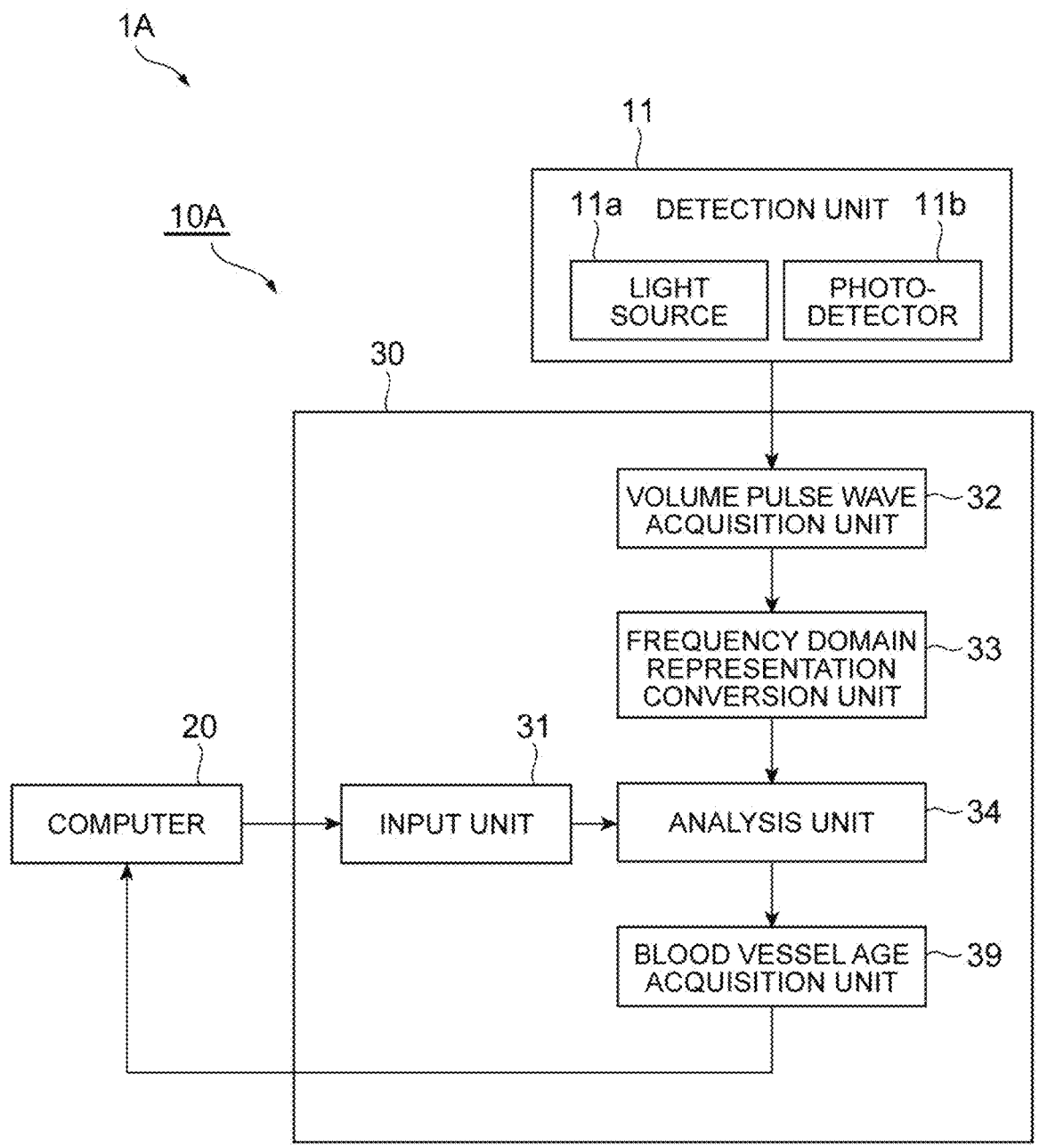
FIG. 14 is a functional block diagram corresponding to FIG. 2 in a blood vessel age estimation system according to a second embodiment.

FIG. 14 is a functional block diagram corresponding to FIG. 2 in the blood vessel age estimation system according to the second embodiment. The blood vessel age estimation system 1A according to the second embodiment includes a computer 20 and a viscoelastic characteristics acquisition device 10A, similar to the blood pressure waveform estimation system 1 according to the first embodiment. The viscoelastic characteristics acquisition device 10A according to this embodiment includes a detection unit 11 and a processing unit 30, similar to the viscoelastic characteristics acquisition device 10 according to the first embodiment. The processing unit 30 of the viscoelastic characteristics acquisition device 10A according to this embodiment includes an input unit 31, a volume pulse wave acquisition unit 32, a frequency domain representation conversion unit 33, and an analysis unit 34, similar to the processing unit 30 of the viscoelastic characteristics acquisition device 10 according to the first embodiment. On the other hand, the processing unit 30 of the viscoelastic characteristics acquisition device 10A according to this embodiment does not include a correction unit 35, a blood pressure ratio calculation unit 36, a time domain representation conversion unit 37, and a blood pressure absolute value calculation unit 38, but instead includes a blood vessel age acquisition unit 39, unlike the processing unit 30 of the viscoelastic characteristics acquisition device 10 according to the first embodiment.

In the blood vessel age estimation system according to this embodiment, the same process as in the first embodiment is performed in the input unit 31, the volume pulse wave acquisition unit 32, the frequency domain representation conversion unit 33, and the analysis unit 34. Accordingly, the viscoelastic characteristic correction value f$_v$ indicating the viscoelastic characteristics is calculated by the analysis unit 34, similar to the first embodiment. The analysis unit 34 outputs the calculated viscoelastic characteristic correction value to the blood vessel age acquisition unit 39.

Figure 15:
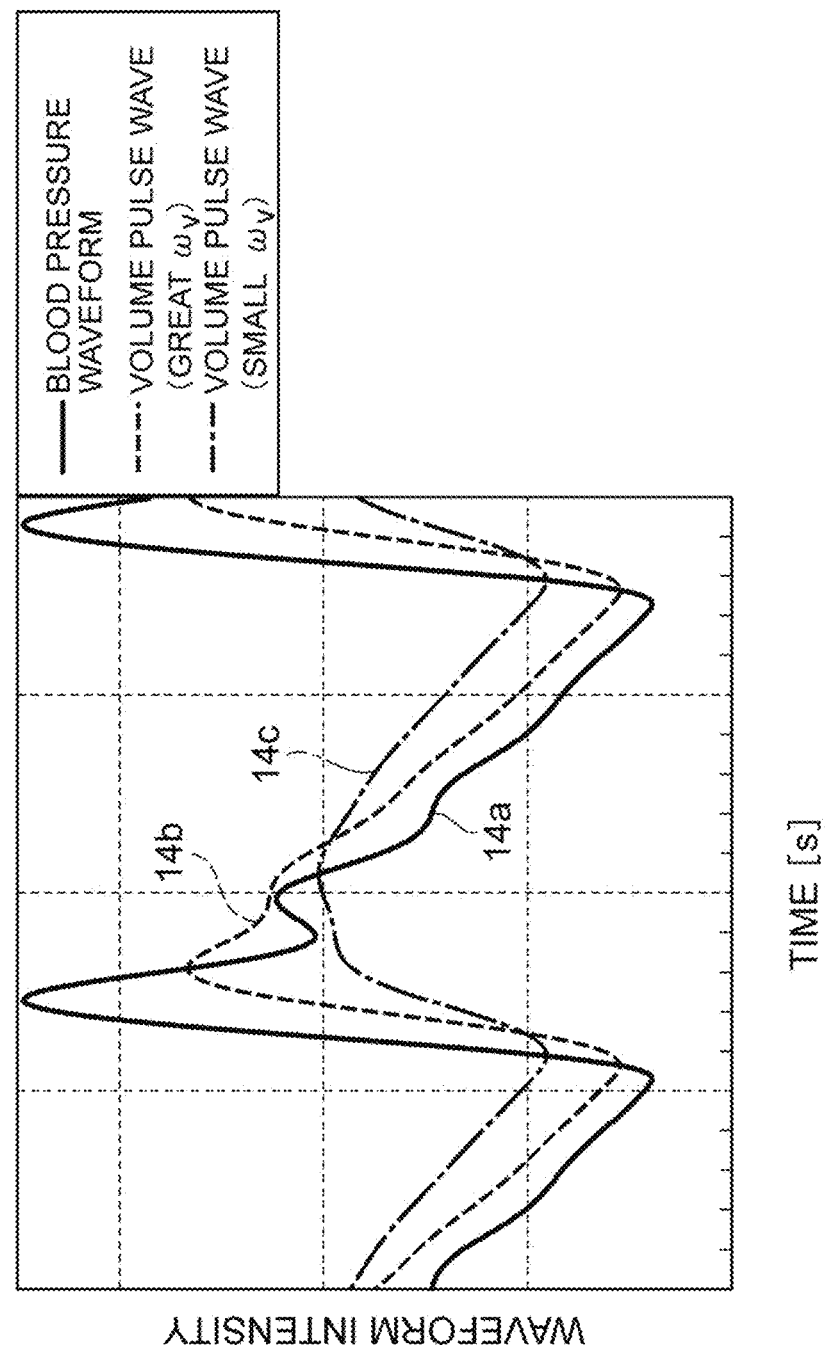
FIG. 15 is a graph showing a relationship between a characteristic frequency of a blood vessel and a volume pulse wave waveform.

The blood vessel age acquisition unit 39 calculates the stiffness β on the basis of the viscoelastic characteristic correction value $f_v$ calculated by the analysis unit 34. The viscoelastic characteristic correction value $f_v$ shows a relationship of $\omega_v=2\pi f_v$ with the characteristic angular frequency $\omega_v$ of the blood vessel. That is, the characteristic angular frequency $\omega_v$ of the blood vessel is indicated by $f_v$. FIG. 15 illustrates a relationship between a characteristic frequency of the blood vessel and the waveform of the volume pulse wave. A horizontal axis of FIG. 15 indicates time, and a vertical axis of FIG. 15 indicates a waveform intensity. A graph 14a in FIG. 15 shows the blood pressure waveform obtained by a catheter type sphygmomanometer or the like, and graphs 14b and 14c in FIG. 15 show the volume pulse wave waveform in the case of the blood pressure waveform shown in the graph 14a. The graph 14b is a volume pulse wave waveform obtained when the characteristic angular frequency $\omega_v$ is high and the graph 14c is a volume pulse wave waveform obtained when the characteristic angular frequency $\omega_v$ is low. Thus, even when the blood pressure waveforms are the same, a degree of bluntness of the volume pulse wave changes according to the magnitude of the characteristic angular frequency $\omega_v$ of the blood vessel in the measurement part. When the characteristic angular frequency $\omega_v$ is lower, the flexibility of the blood vessel is shown to increase. That is, in the graph 14b and the graph 14c, the graph 14c having a blunter waveform is shown to indicate a more flexible blood vessel.

That is, the characteristic angular frequency $\omega_v$ of the blood vessel indicated by the viscoelastic characteristic correction value $f_v$ is an indicator showing a degree of flexibility of the blood vessel. Therefore, the hardness of the blood vessel can be evaluated by comparing the magnitude of the characteristic angular frequency $\omega_v$ instead of the stiffness $\beta$ of the related art.

Figure 16:
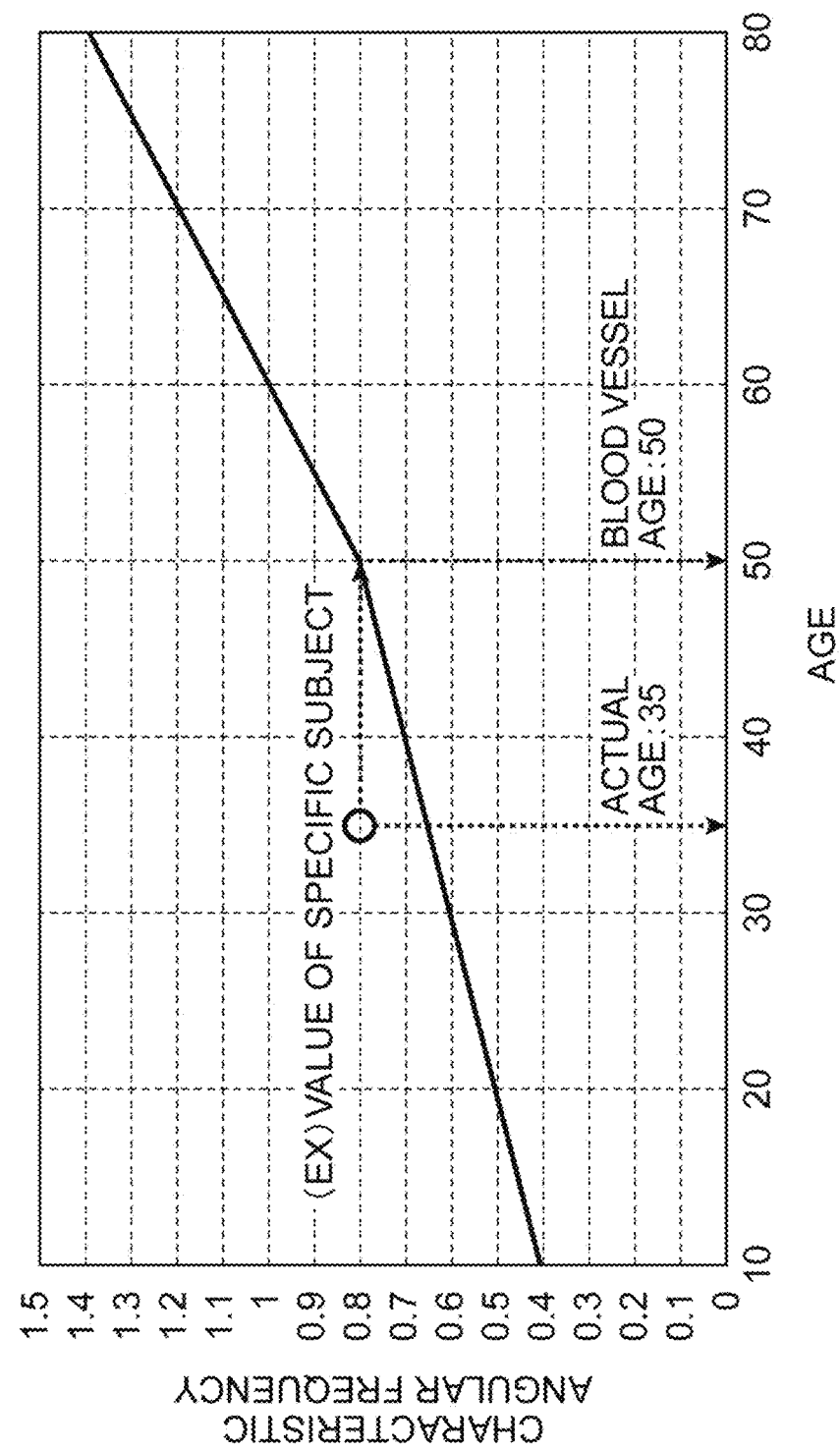
FIG. 16 is a graph showing a correspondence between an age and a characteristic angular frequency.

The blood vessel age acquisition unit 39 acquires the blood vessel age using the correspondence relationship between the age and the characteristic angular frequency $\omega_v$ as illustrated in FIG. 16, for example. FIG. 16 illustrates a graph showing a statistical result of the average value of the characteristic angular frequency $\omega_v$ for each age. A horizontal axis of FIG. 16 indicates the age, and a vertical axis of FIG. 16 indicates the characteristic angular frequency $\omega_v$. The graph of FIG. 16 is created on the basis of, for example, data collected for a plurality of subjects in advance. The blood vessel age acquisition unit 39 records the correspondence relationship between the age and the characteristic angular frequency $\omega_v$ as shown in the graph of FIG. 16 in advance. When the characteristic angular frequency $\omega_v$ indicated by the viscoelastic characteristic correction value $f_v$ calculated by the analysis unit 34 for a specific subject whose actual age is 35 years, for example, is 0.8, the blood vessel age acquisition unit 39 acquires information indicating that the blood vessel age corresponding to the characteristic angular frequency $\omega_v$ is 50 years with reference to the correspondence relationship shown in the graph of FIG. 16.

Figure 17:
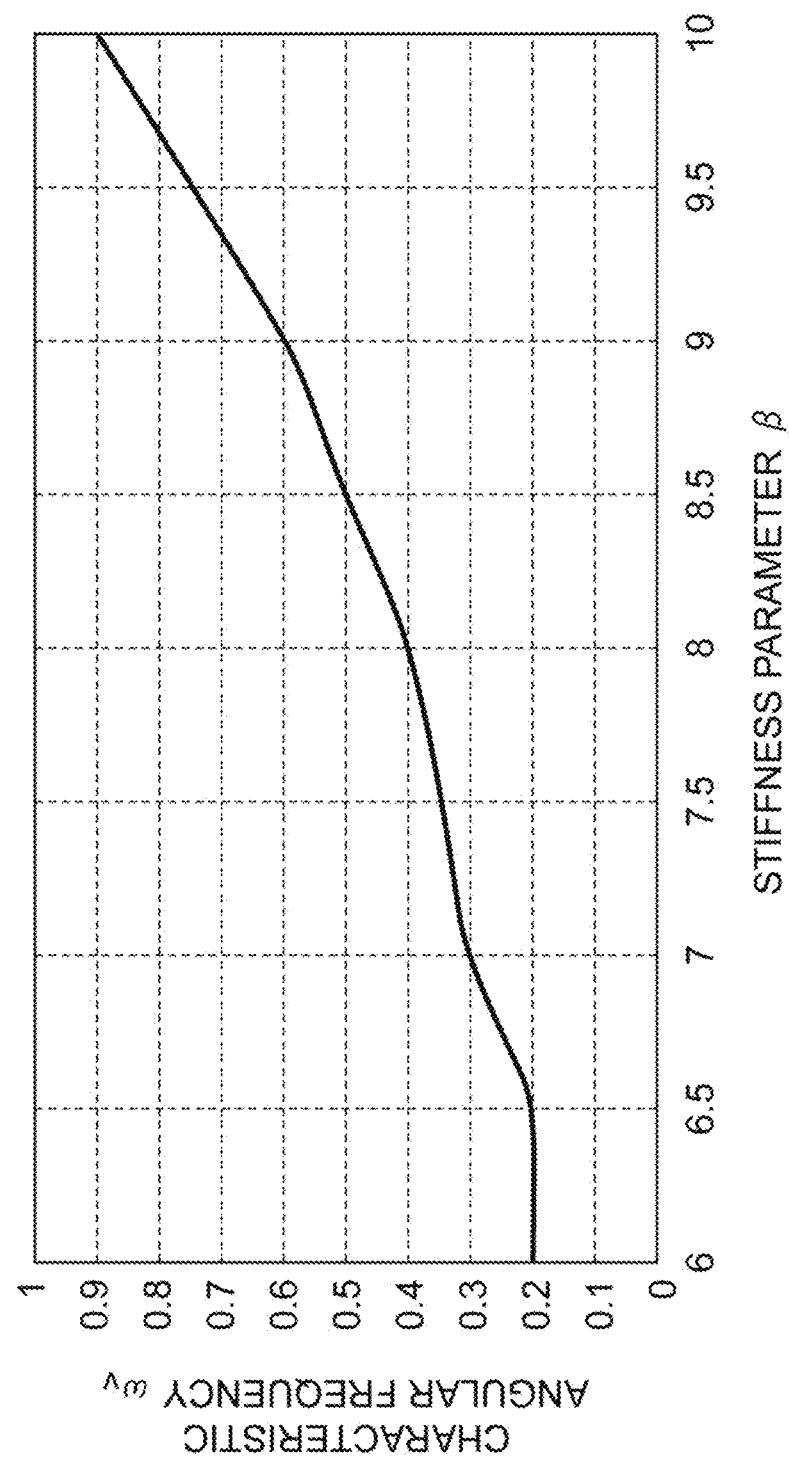
FIG. 17 is a graph showing a correlation between stiffness and a characteristic angular frequency.

Further, by collecting the value of the stiffness $\beta$ when collecting data to create a graph as illustrated in FIG. 16, a correlation graph between the stiffness $\beta$ and the characteristic angular frequency $\omega_v$ as illustrated in FIG. 17 may be created. A horizontal axis of FIG. 17 indicates the stiffness $\beta$, and a vertical axis of FIG. 17 indicates the characteristic angular frequency $\omega_v$. The blood vessel age acquisition unit 39 may record the correspondence relationship between the stiffness $\beta$ and the characteristic angular frequency $\omega_v$ as shown in the correlation graph of FIG. 17 in advance. In this case, the blood vessel age acquisition unit 39 can obtain the stiffness $\beta$ from the characteristic angular frequency $\omega_v$ with reference to such a correspondence relationship between the stiffness $\beta$ and the characteristic angular frequency $\omega_v$, obtain the blood vessel age from the stiffness $\beta$, and increase a credibility of the acquired blood vessel age.

Further, in addition to the method of acquiring the blood vessel age on the basis of the correspondence relationship as illustrated in FIG. 16 or 17, that is, the above-described statistical scheme, the blood vessel age acquisition unit 39 may acquire the blood vessel age on the basis of the stiffness $\beta$ by obtaining the stiffness $\beta$ from the characteristic angular frequency $\omega_v$ in numerical calculation. Hereinafter, a method of acquiring the blood vessel age in numerical calculation using the blood vessel age acquisition unit 39 will be described in detail.

Figure 18:
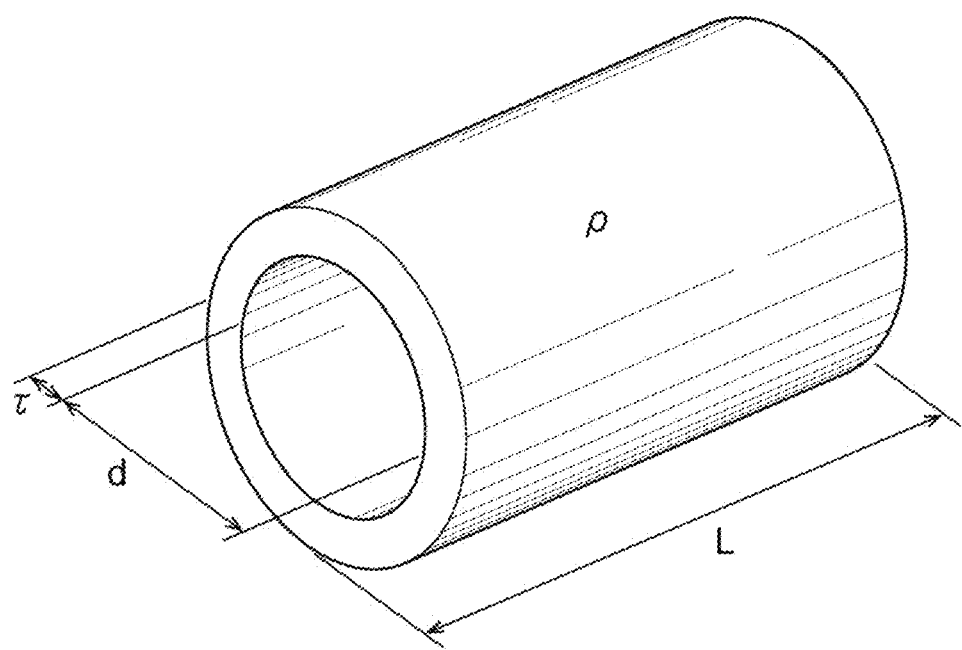
FIG. 18 is a schematic diagram of a blood vessel that is a measurement target for stiffness.

FIG. 18 illustrates a schematic diagram of the blood vessel that is a measurement target of the stiffness $\beta$. In the blood vessel illustrated in FIG. 18, $\tau$ is a thickness of the blood vessel, d is an inner diameter of the blood vessel, $\rho$ is a density of the blood vessel, and L is a length of the blood vessel. The thickness $\tau$ of the blood vessel is assumed to be sufficiently smaller than the inner diameter d of the blood vessel. A case in which the blood pressure p changing with a pumping motion of the heart from the inside is applied to the blood vessel of FIG. 18 and the inner diameter d changes is considered.

Figure 19:
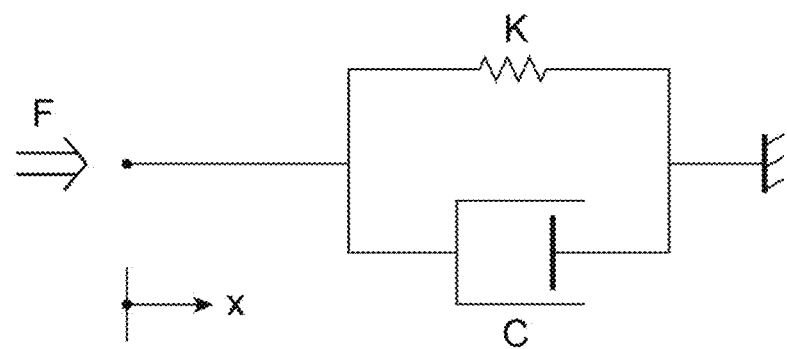
FIG. 19 is a diagram illustrating a parallel spring damper model.

In this embodiment, for example, a parallel spring damper model illustrated in FIG. 19 is used as a blood vessel model indicating a relationship between blood pressure exerted on the inner wall of the blood vessel and an inner diameter displacement. As the blood vessel model, a series spring damper model as illustrated in a part (a) of FIG. 20 may be used, or a series and parallel hybrid model as illustrated in a part (b) of FIG. 20 may be used. Further, in this embodiment, since an influence of the blood vessel mass is very small, the influence is considered to be negligible, but a part indicating an influence of the blood vessel mass M may be added in such a blood vessel model.

In the blood vessel model illustrated in FIG. 19 or 20, F is a force exerted on the inner wall of the blood vessel by the blood pressure p, K is an equivalent stiffness of the blood vessel, C is an equivalent damping coefficient of the blood vessel, and x is a displacement of a point at which F is exerted in the blood vessel model. A displacement x corresponds to an amount of change $\Delta d$ in the inner diameter d of the blood vessel in the schematic view of FIG. 18. A subscript is a suffix for convenience.

In various blood vessel models, a relationship between a Fourier transform value P of the blood pressure p and the Fourier transform value X of the displacement x can be generalized by Equation (6) below using a transfer function G.

[Math. 6]

$$P = G \cdot X \quad (6)$$

In the blood vessel model illustrated in FIG. 19, a relationship between the blood pressure p and the displacement x in the time domain is shown in Equation (7) below. In Equation (7) below, f(t) is the force exerted on the inner wall of the blood vessel due to the blood pressure p(t), and S is a surface area of the inner wall of the blood vessel. As described above, K is an equivalent stiffness of the blood vessel, and C is an equivalent damping coefficient of the blood vessel.

[Math. 7]

$$f(t) = p(t) \cdot S = Kx(t) + C\frac{\partial x(t)}{\partial t} \quad (7)$$

By performing Fourier-transform on and rearranging Equation (7) above, Equation (8) below is obtained. In Equation (8) below, $\omega_v$ is the characteristic angular frequency and $\zeta$ is a damping ratio.

[Math. 8]

$$P = \frac{\rho\tau\omega_v^2}{4}\left(1 + \frac{2\zeta\omega}{\omega_v}i\right)X \tag{8}$$

The characteristic angular frequency $\omega_v$ and a damping ratio $\zeta$ are shown in Equations (9) and (10) below, respectively.

[Math. 9]

$$\omega_v = \sqrt{\frac{K}{M}} \tag{9}$$

$$\zeta = \frac{C}{2\sqrt{MK}} \tag{10}$$

Further, the blood vessel mass M and the surface area S of the inner wall of the blood vessel are approximated by Equations (11) and (12) using a representative value $d_r$ of the inner diameter assuming that the thickness $\tau$ of the blood vessel is sufficiently smaller than the inner diameter d of the blood vessel.

[Math. 10]

$$S = 2\pi d_r L \tag{11}$$

$$M = \rho L\pi[(d_r+\tau)^2 - d_r^2]/4 \approx \rho L\pi \cdot d_r \cdot \tau/2 \tag{12}$$

Thus, the blood vessel model illustrated in FIGS. 19 and 20 is in the form in which the characteristic angular frequency $\omega_v$ of the blood vessel is included in the transfer function G Further, among variables included in the transfer function G, there are anatomical statistical values in a density $\rho$ of the blood vessel or the thickness $\tau$ of the blood vessel, and the damping ratio $\zeta$ can be treated as substantially a constant irrespective of an age. Therefore, by utilizing existing statistical values, the transfer function G of the blood vessel can be calculated on the basis of the characteristic angular frequency $\omega_v$ indicated by the viscoelastic characteristic correction value $f_v$ calculated by the analysis unit. When the transfer function G is calculated, the Fourier transform value X of the displacement x is shown as Equation (13) below using an inverse function $G^{-1}$ of the transfer function G and the Fourier transform value P of the blood pressure obtained on the basis of the volume pulse wave using a scheme such as the blood pressure estimation method in the first embodiment.

[Math. 11]

$$G^{-1} \cdot P = X \tag{13}$$

By performing an inverse Fourier transform on Equation (13) to convert Equation (13) into a time domain equation, a time transition x(t) of the displacement x of the blood vessel wall can be obtained. By adding a statistically obtained initial radius d0 of the blood vessel to x(t), a time transition d(t) of an blood vessel inner diameter is obtained by Equation (14) below.

[Math. 12]

$$d(t) = d0 + 2x(t) \tag{14}$$

The stiffness $\beta$ can be obtained in numerical calculation by calculating Equation (15) below from d(t) obtained by Equation (14) above and applying the value to Equation (5) above. Therefore, by comparing the stiffness $\beta$ with an existing average value of the stiffness $\beta$ for each age, it becomes possible to acquire the blood vessel age.

[Math. 13]

$$\frac{d}{\Delta d} = \frac{\min\{d(t)\}}{\max\{d(t)\} - \min\{d(t)\}} \tag{15}$$

As described above, in this embodiment, since the viscoelastic characteristic correction value $f_v$ indicating the viscoelastic characteristics is calculated, it is possible to evaluate the cardiovascular system conveniently, sufficiently, and accurately on the basis of the viscoelastic characteristic correction value $f_v$. In particular, according to this embodiment, the blood vessel age acquisition unit 39 acquires the vessel age of the inspection target on the basis of the viscoelastic characteristic correction value $f_v$ (blood vessel age acquisition step). Therefore, it is possible to evaluate the acquired blood vessel age conveniently and accurately.

Although various embodiments of the present invention have been described above, the present invention is not limited to the above-described embodiments, and may be modified without departing from the gist described in each claim or may be applied to other ones.

For example, in the blood pressure waveform estimation system 1 according to the first embodiment, the viscoelastic characteristics acquisition device 10 is the viscoelastic characteristics acquisition device, but the present invention is not limited thereto. For example, in the blood pressure waveform estimation system 1, a configuration including the computer 20 in addition to the viscoelastic characteristics acquisition device 10 may be a viscoelastic characteristics acquisition device. The computer 20 may be a viscoelastic characteristics acquisition device in place of the viscoelastic characteristics acquisition device 10. When the computer 20 is the viscoelastic characteristics acquisition device, the computer 20 has each function of the processing unit 30 described above. Further, for example, in the blood pressure waveform estimation system 1, the computer 20 and the processing unit 30 may be integrally configured.

Figure 21:
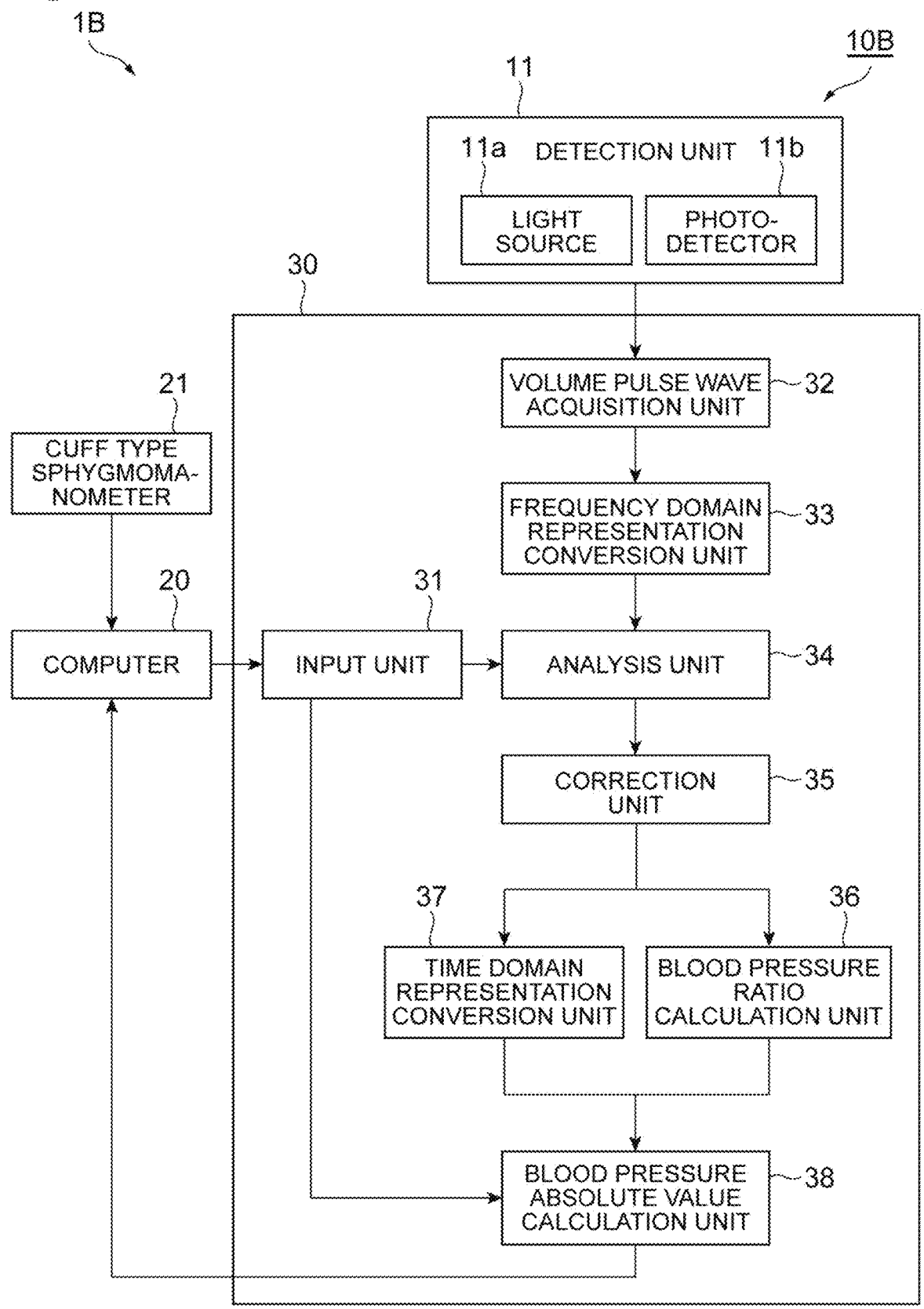
FIG. 21 is a functional block diagram corresponding to FIG. 2 in a blood pressure estimation system according to a modification example.

Further, for example, as illustrated in FIG. 21, the blood pressure waveform estimation system 1B according to the modification example may include a cuff type sphygmomanometer 21 (blood pressure measurement unit) that measures values corresponding to the maximum blood pressure and the minimum blood pressure of the inspection target. FIG. 21 is a functional block diagram corresponding to FIG. 2 in the blood pressure waveform estimation system 1B according to the modification example. In this case, the values corresponding to the maximum blood pressure and the minimum blood pressure measured by the cuff type sphygmomanometer 21 are output to the input unit 31 via the computer 20, for example. Further, the cuff type sphygmomanometer 21 may be included in the viscoelastic characteristics acquisition device 10B itself included in the blood pressure waveform estimation system 1B, or the values corresponding to the maximum blood pressure and the minimum blood pressure measured by the cuff type sphygmomanometer may be output directly from the cuff type sphygmomanometer 21. In this case, the values corresponding to the maximum blood pressure and the minimum blood pressure of the inspection target input to the input unit 31 can be easily acquired through measurement of the cuff type sphygmomanometer 21 included in the viscoelastic characteristics acquisition device 10B without providing a device for measuring the values separately from the viscoelastic characteristics acquisition device 10B. A catheter type sphygmomanometer or the like may be used in place of the cuff type sphygmomanometer 21.

Figure 22:
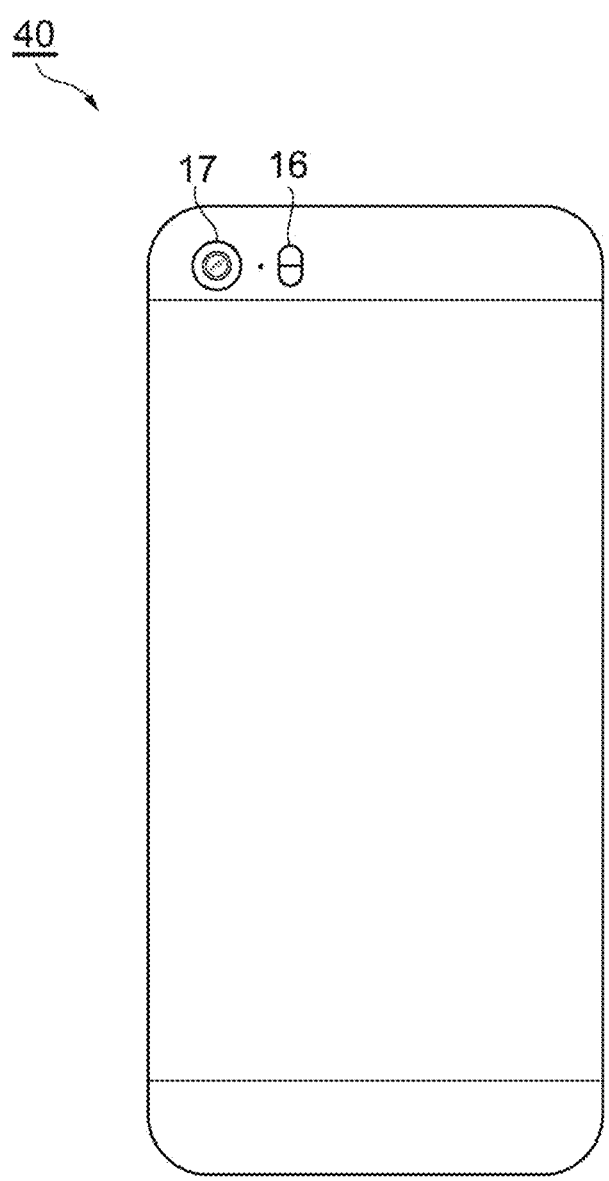
FIG. 22 is a schematic configuration diagram illustrating a viscoelastic characteristics acquisition device according to a modification example.

Further, for example, as illustrated in FIG. 22, the viscoelastic characteristics acquisition device 10 may be configured as a communication terminal 40 such as a smartphone. A communication terminal such as a smartphone is included in a computer including a processor, a storage medium, or the like. In this modification example, the communication terminal 40 has the same functions as the viscoelastic characteristics acquisition devices 10, 10A, and 10B according to the above embodiment. Further, the communication terminal 40 may have each function of the computer 20, in addition to each function of the viscoelastic characteristics acquisition device 10. That is, each function of the viscoelastic characteristics acquisition device 10 according to the first embodiment and each function of the computer 20 may be realized in an integrated configuration.

The communication terminal 40 differs from the viscoelastic characteristics acquisition devices 10, 10A, and 10B in that the detection unit 11 includes a light source 16 in place of the light source 11a, and a photodetector 17 in place of the photodetector 11b. The light source 16 is, for example, a flash lamp of the communication terminal 40. The photodetector 17 is, for example, a camera of the communication terminal 40. That is, in this embodiment, a function originally included in the communication terminal 40 also serves as a detection unit. Further, the communication terminal 40 may include the light source 16 and the photodetector 17 separately from the flash lamp or the camera. Further, a tablet computer or the like may also be included as a computer having a processor, a storage medium, or the like, and a tablet computer or the like may be used in place of the communication terminal 40.

In this modification example, in a state in which a surface (for example, a finger) of the living body H that is a subject is placed on both the light source 16 and the photodetector 17 of the communication terminal 40, light from the light source 16 is radiated from the surface of the living body H to the inside. Reflected light from the living body H is detected by the photodetector 17 and output to the volume pulse wave acquisition unit 32. Accordingly, the volume pulse wave acquisition unit 32 acquires the volume pulse wave. Subsequently, the volume pulse wave acquisition unit 32 acquires a pulse waveform on the basis of the acquired volume pulse wave, as in the above embodiment. The viscoelastic characteristics are acquired through the same process as in the above embodiment. Thus, in this modification example, the cardiovascular system can also be evaluated on the basis of viscoelastic characteristics conveniently, sufficiently, and accurately. Further, according to this embodiment, the function as the viscoelastic characteristics acquisition device can be realized by the function originally included in the communication terminal 40, which is convenient.

Figure 23:
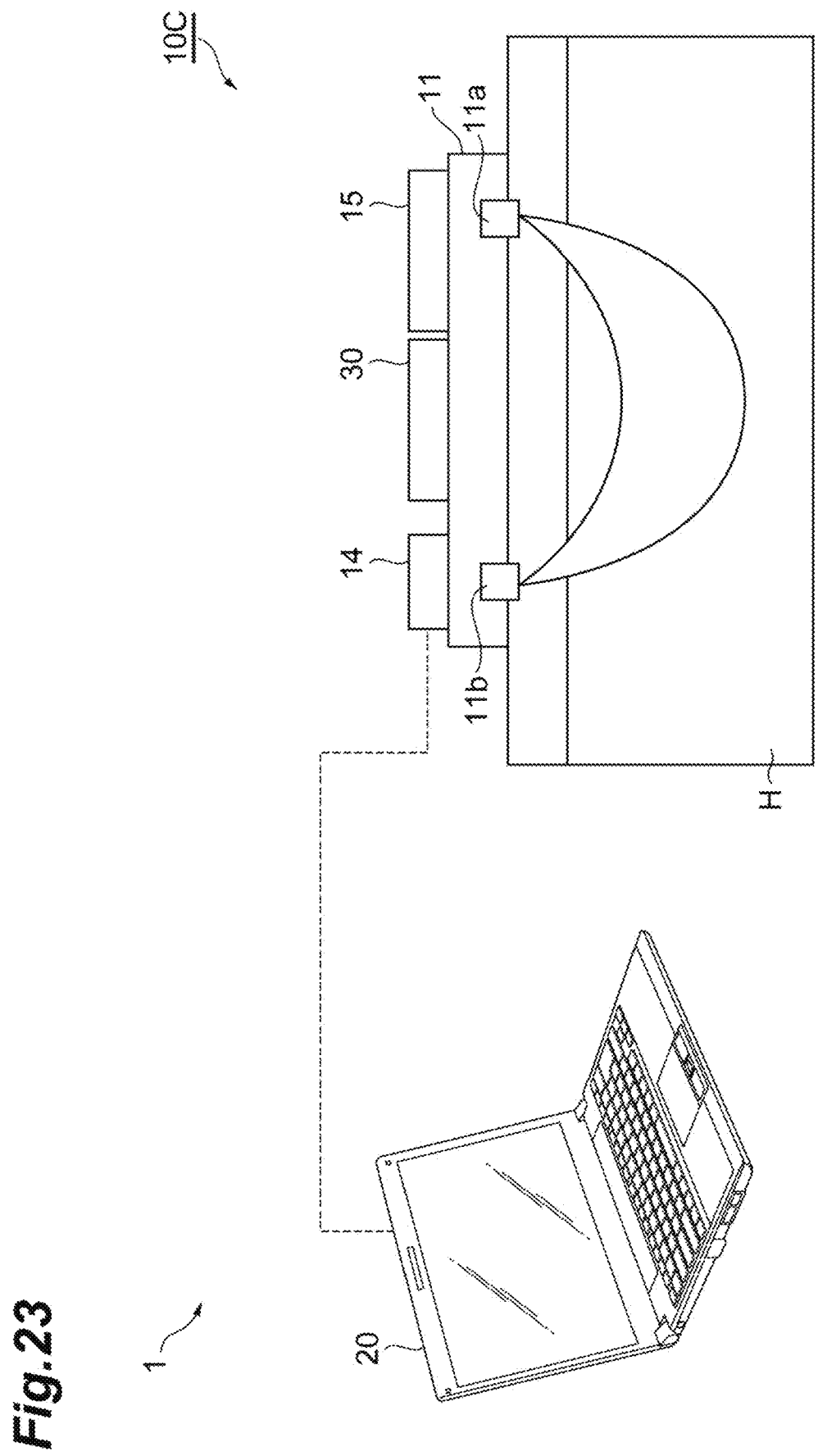
FIG. 23 is a schematic configuration diagram illustrating a viscoelastic characteristics acquisition device according to a modification example.

Further, for example, as illustrated in FIG. 23, the viscoelastic characteristics acquisition device 10C may be configured by integrating the detection unit 11 and the processing unit 30. The viscoelastic characteristics acquisition device 10C is attached to the surface of the living body H, and integrally includes, for example, a communication unit 14, a processing unit 30, a power supply unit 15, and a detection unit 11 including a light source 11a and a photodetector 11b. In the viscoelastic characteristics acquisition device 10C according to this modification example, viscoelastic characteristics can be acquired, similar to the above embodiment.

Further, the surface of the living body H that is the subject may be a part other than a palm or a finger, or may be a forehead, an upper arm, a neck, an earlobe, or the like.

Figure 24:
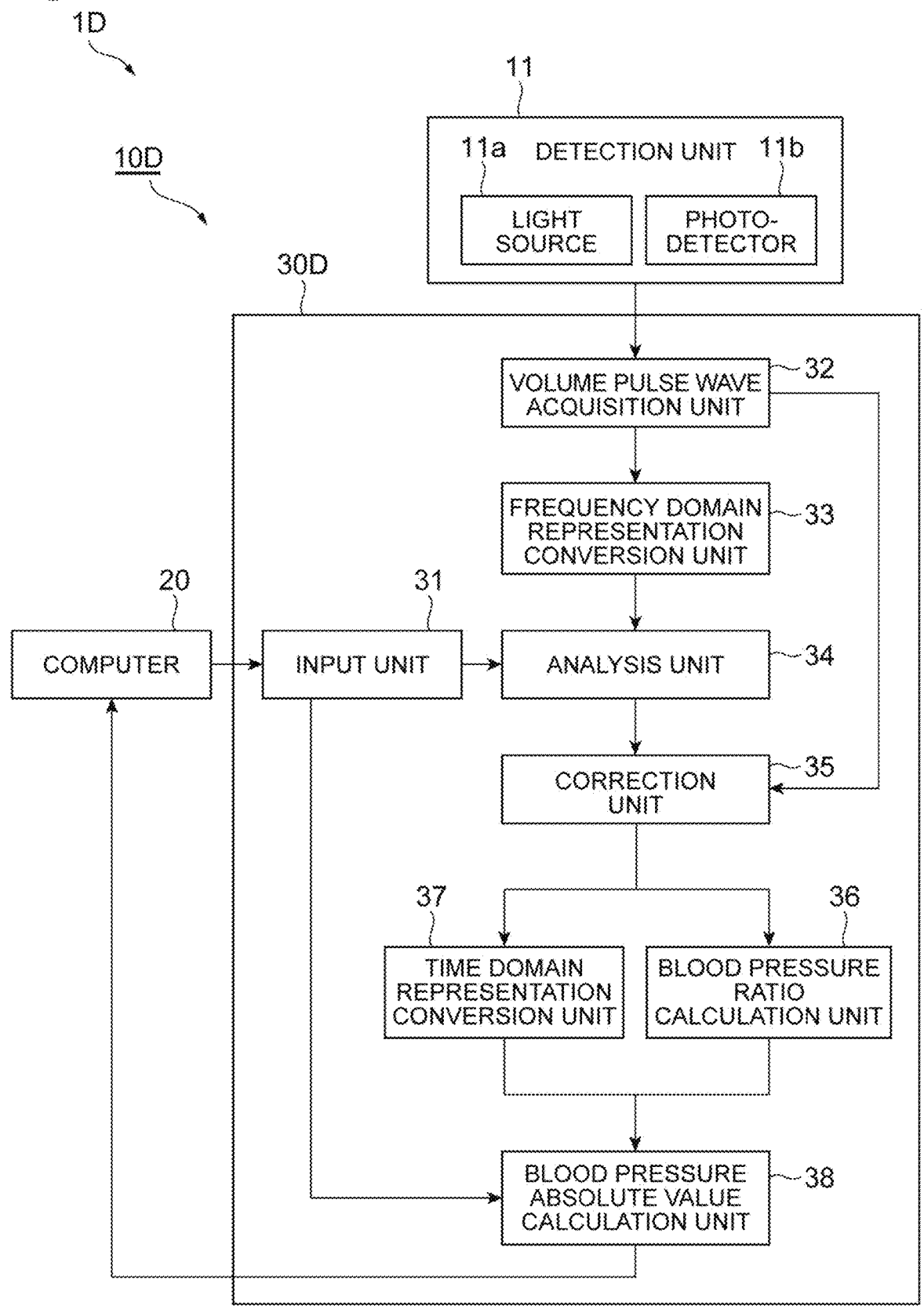
FIG. 24 is a schematic configuration diagram illustrating a viscoelastic characteristics acquisition device according to a modification example.

Further, although the volume pulse wave $LW_T$ acquired by the volume pulse wave acquisition unit 32 is corrected with the viscoelastic characteristic correction value fv in the frequency domain, and the similar blood pressure waveform $P'_T$ is calculated in the frequency domain representation conversion unit 33, the correction unit 35, and the time domain representation conversion unit 37 as described above in the first embodiment, the volume pulse wave $LW_T$ may be corrected with the viscoelastic characteristic correction value fv in the time domain, and the similar blood pressure waveform $P'_T$ may be calculated. For example, as in the processing unit 30D in the viscoelastic characteristics acquisition device 10D illustrated in FIG. 24, in the configuration in which the volume pulse wave acquisition unit 32 and the correction unit 35 are electrically connected to each other and the volume pulse wave $LW_T$ is input from the volume pulse wave acquisition unit 32 to the correction unit 35, a filter $F_v$ based on the viscoelastic characteristic correction value $f_v$ is generated in the analysis unit 34, and the filter $F_v$ is input from the analysis unit 34 to the correction unit 35. The similar blood pressure waveform $P'_T$ may be obtained by correcting the volume pulse wave $LW_T$ in the time domain with the filter $F_v$ corresponding to the viscoelastic characteristic correction value $f_v$ in the correction unit 35.

Further, as a result of intensive research, the present inventors have newly found that, when the wave at the frequency corresponding to the pulse is set as the first harmonic wave and the wave at the frequency that is n times (n is a positive integer) the frequency of the first harmonic wave is set as an n-th harmonic wave in the volume pulse wave spectrum, a relationship that a ratio of the sum of the intensities of the volume pulse wave spectra including the respective intensities of at least the first harmonic wave to the third harmonic wave and the intensity of the first harmonic wave is substantially equal to the ratio of the maximum blood pressure value and the minimum blood pressure value is established. On the basis of this, the present inventors have conceived that the viscoelastic characteristics of the blood vessel can be derived accurately on the basis of the values corresponding to the maximum blood pressure and the minimum blood pressure and the sum of intensities of the volume pulse wave spectra including the intensities of the respective volume pulse wave spectra of at least the first harmonic wave to the third harmonic wave. That is, in the viscoelastic characteristics acquisition device according to the above embodiment, when the wave at the frequency corresponding to the pulse is set as the first harmonic wave and the wave at the frequency that is n times (n is a positive integer) the frequency of the first harmonic wave is set as an n-th harmonic wave in the volume pulse wave spectrum, the analysis unit may acquire the viscoelastic characteristics on the basis of the values corresponding to the maximum blood pressure and the minimum blood pressure and the sum of intensities of the volume pulse wave spectra including the intensities of the respective volume pulse wave spectra of at least the first harmonic wave to the third harmonic wave. Further, in the viscoelastic characteristics acquisition method according to the above embodiment, when the wave at the frequency corresponding to the pulse is set as the first harmonic wave and the wave at the frequency that is n times (n is a positive integer) the frequency of the first harmonic wave is set as an n-th harmonic wave in the volume pulse wave spectrum, the analysis step may include acquiring the viscoelastic characteristics on the basis of the values corresponding to the maximum blood pressure and the minimum blood pressure and the sum of intensities of the volume pulse wave spectra including the intensities of the respective volume pulse wave spectra of at least the first harmonic wave to the third harmonic wave.

Further, as a result of further repeated intensive research, the present inventors have conceived that, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the volume pulse wave spectrum, the same correspondence relationship as above is established by setting the intensity of each spread n-th harmonic wave to the intensity of the n-th harmonic wave group even in a case in which each n-th harmonic wave spreads in a Gaussian shape in a frequency direction due to the influence of biological fluctuation. On the basis of this, the present inventors have conceived that the viscoelastic characteristics of the blood vessel can be accurately derived on the basis of the values corresponding to the maximum blood pressure and the minimum blood pressure, and the sum of the intensities of the volume pulse wave spectra including the intensities of the respective volume pulse wave spectra of at least the first harmonic wave group to the third harmonic wave group. That is, in the viscoelastic characteristics acquisition device according to the above embodiment, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times the frequency corresponding to the pulse, is set as an n-th harmonic wave group in the volume pulse wave spectrum, the analysis unit may acquire the viscoelastic characteristics on the basis of the values corresponding to the maximum blood pressure and the minimum blood pressure, and the sum of the intensities of the volume pulse wave spectra including the intensities of the respective volume pulse wave spectra of at least the first harmonic wave group to the third harmonic wave group. Further, in the viscoelastic characteristics acquisition method according to the above-described embodiment, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the volume pulse wave spectrum, the analysis step may include acquiring the viscoelastic characteristics on the basis of the values corresponding to the maximum blood pressure and the minimum blood pressure, and the sum of the intensities of the volume pulse wave spectra including the intensities of the respective volume pulse wave spectra of at least the first harmonic wave group to the third harmonic wave group.

In the viscoelastic characteristics acquisition device and the viscoelastic characteristics acquisition method according to the above embodiment, the values corresponding to the maximum blood pressure and the minimum blood pressure may be a maximum blood pressure value and a minimum blood pressure value.

In the viscoelastic characteristics acquisition device and the viscoelastic characteristics acquisition method according to the above embodiment, the values corresponding to the maximum blood pressure and the minimum blood pressure may be a ratio of the maximum blood pressure value to the minimum blood pressure value.

The viscoelastic characteristics acquisition device according to the above embodiment further may include a blood pressure measurement unit for measuring values corresponding to a maximum blood pressure and a minimum blood pressure of an inspection target, and the blood pressure measurement unit may output values corresponding to the measured maximum blood pressure and minimum blood pressure to the input unit. In this case, the values corresponding to the maximum blood pressure and the minimum blood pressure of the inspection target to be input to the input unit may be easily acquired through measurement of the blood pressure measurement unit without providing a device for measuring the values separately from the viscoelastic characteristics acquisition device.

The pulse wave acquisition unit may include an irradiation device for irradiating the inside of the living body with light, and a photodetector for detecting the light transmitted through the inside of the living body. In this case, by detecting the light radiated from the irradiation device included in the pulse wave acquisition unit and transmitted through the inside of the living body using the photodetector included in the pulse wave acquisition unit, it is possible to easily obtain a waveform corresponding to the volume pulse wave without separately providing a device that detects a signal for acquiring a time waveform corresponding to the volume pulse wave separately from the viscoelastic characteristics acquisition device.

The viscoelastic characteristics acquisition device according to the above embodiment may include a correction unit for correcting a time waveform corresponding to a volume pulse wave on the basis of the viscoelastic characteristics acquired by the analysis unit, and a blood pressure waveform acquisition unit for acquiring the blood pressure waveform of the inspection target on the basis of the time waveform corrected by the correction unit. Further, the viscoelastic characteristics acquisition method according to the above embodiment may include a correction step of correcting a time waveform corresponding to a volume pulse wave on the basis of the viscoelastic characteristics acquired in the analysis step, and a blood pressure waveform acquisition step of acquiring the blood pressure waveform of the inspection target on the basis of the time waveform corrected in the correction step. In this case, the time waveform based on the volume pulse wave is corrected on the basis of the viscoelastic characteristics indicating the relationship between the volume pulse wave and the blood pressure waveform, and the blood pressure waveform is acquired on the basis of the corrected time waveform. Thus, the blood pressure waveform can be accurately estimated from the time waveform corresponding to the volume pulse wave, and the cardiovascular system can be evaluated on the basis of the estimated blood pressure waveform conveniently, sufficiently, and accurately.

The viscoelastic characteristics acquisition device according to the above embodiment may further include a blood vessel age acquisition unit for acquiring a blood vessel age of the inspection target on the basis of the viscoelastic characteristics acquired by the analysis unit. The viscoelastic characteristics acquisition method according to the above embodiment may further include a blood vessel age acquisition step of acquiring a blood vessel age of the inspection target on the basis of the viscoelastic characteristics acquired in the analysis step. In this case, since the blood vessel age of the inspection target is acquired on the basis of the viscoelasticity characteristics indicating the viscoelasticity of the blood vessel, the cardiovascular system can be evaluated on the basis of the acquired blood vessel age conveniently, sufficiently, and accurately.

INDUSTRIAL APPLICABILITY

According to the aspect of the present invention, the viscoelastic characteristics acquisition device, the viscoelastic characteristics acquisition method, the viscoelastic characteristics acquisition program, and the recording medium having the program recorded thereon are adopted as use forms, and it is possible to evaluate the cardiovascular system conveniently, sufficiently, and accurately.

REFERENCE SIGNS LIST 10, 10A, 10B, 10C, 10D: viscoelastic characteristics acquisition device
11: detection unit (pulse wave acquisition unit)
11a, 16: light source (irradiation device)
11b, 17: photodetector
21: cuff type sphygmomanometer (blood pressure measurement unit)
31: input unit
32: volume pulse wave acquisition unit (pulse wave acquisition unit)
33: frequency domain representation conversion unit (spectrum acquisition unit)
34: analysis unit
35 correction unit
36: blood pressure ratio calculation unit (blood pressure waveform acquisition unit)
37: time domain representation conversion unit (blood pressure waveform acquisition unit)
38: blood pressure absolute value calculation unit (blood pressure waveform acquisition unit)
39: blood vessel age acquisition unit
40: communication terminal (viscoelastic characteristics acquisition device)
H: living body
P1: viscoelastic characteristics acquisition program.

The invention claimed is:

1. A system for acquiring viscoelastic characteristics of a blood vessel of an inspection target, the system comprising:
a non-transitory computer-readable recording medium that stores instructions for acquiring viscoelastic characteristics of the blood vessel of the inspection target; and
a processor configured to execute the instructions including:
acquire a time waveform corresponding to a volume pulse wave of the inspection target,
perform Fourier transform on the time waveform and acquire a volume pulse wave spectrum,
acquire a maximum blood pressure value of the inspection target and a minimum blood pressure value of the inspection target,
calculate the viscoelastic characteristics on the basis of acquired maximum blood pressure value, the acquired minimum blood pressure value, and the volume pulse wave spectrum at frequency bands equal to or higher than a frequency corresponding to a pulse of the inspection target,
correct a time waveform corresponding to the volume pulse wave on the basis of the viscoelastic characteristics, and
estimate, in real time, a blood pressure waveform of the inspection target on the basis of the time waveform.

2. The system according to claim 1, wherein the instruction to calculate the viscoelastic characteristics includes:
when a wave at the frequency corresponding to the pulse is set as a first harmonic wave, and a wave at a frequency that is n times (n is a positive integer) the frequency of the first harmonic wave is set as an n-th harmonic wave in the volume pulse wave spectrum, calculate the viscoelastic characteristics on the basis of the acquired maximum blood pressure value, the acquired minimum blood pressure value, and a sum of intensities of the volume pulse wave spectra including the intensities of the respective volume pulse wave spectra of at least the first harmonic wave to a third harmonic wave.

3. The system according to claim 1, wherein the instruction to calculate the viscoelastic characteristics includes:
when a group of waves at a frequency in a predetermined range equal to or higher than the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the volume pulse wave spectrum, calculate the viscoelastic characteristics on the basis of the acquired maximum blood pressure value, the acquired minimum blood pressure value, and a sum of intensities of the volume pulse wave spectra including the intensities of the respective volume pulse wave spectra of at least the first harmonic wave group to the third harmonic wave group.

4. The system according to claim 1, wherein the acquired maximum blood pressure value and the acquired minimum blood pressure value are a ratio of the maximum blood pressure value of the inspection target to the minimum blood pressure value of the inspection target.

5. The system according to claim 1, further comprising:
a blood pressure measurement device configured to measure the maximum blood pressure value of the inspection target and the minimum blood pressure value of the inspection target,
wherein the blood pressure measurement device outputs the measured maximum blood pressure value and the measured minimum blood pressure value to the processor.

6. The system according to claim 1, further comprising:
an irradiation device configured to irradiate an inside of a living body with light, and a photodetector configured to detect the light transmitted through the inside of the living body.

7. The system according to claim 1, wherein the processor is further configured to execute the instructions including:
   estimate a blood vessel age of the inspection target on the basis of the viscoelastic characteristics.

8. A computer-implemented method of acquiring viscoelastic characteristics of a blood vessel of an inspection target, the method comprising:
   acquiring a time waveform corresponding to a volume pulse wave of the inspection target;
   performing Fourier transform on the time waveform and acquiring a volume pulse wave spectrum;
   acquiring a maximum blood pressure value of the inspection target and a minimum blood pressure value of the inspection target;
   calculating the viscoelastic characteristics on the basis of the acquired maximum blood pressure value, the acquired minimum blood pressure value, and the volume pulse wave spectrum at frequency bands equal to or higher than a frequency corresponding to a pulse of the inspection target;
   correcting a time waveform corresponding to a volume pulse wave on the basis of the viscoelastic characteristics; and
   estimating, in real time, a blood pressure waveform of the inspection target on the basis of the time waveform.

9. The method according to claim 8, wherein calculating the viscoelastic characteristics includes:
   when a wave at the frequency corresponding to the pulse is set as a first harmonic wave, and a wave at a frequency that is n times (n is a positive integer) the frequency of the first harmonic wave is set as an n-th harmonic wave in the volume pulse wave spectrum, calculating the viscoelastic characteristics on the basis of the acquired maximum blood pressure value, the acquired minimum blood pressure value, and a sum of intensities of volume pulse wave spectra including the intensities of the respective volume pulse wave spectra of at least the first harmonic wave to a third harmonic wave.

10. The method according to claim 8, wherein calculating the viscoelastic characteristics includes:
   when a group of waves at the frequency in a predetermined range equal to or higher than the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the volume pulse wave spectrum, calculating the viscoelastic characteristics on the basis of the acquired maximum blood pressure value, the acquired minimum blood pressure value, and a sum of intensities of the volume pulse wave spectra including the intensities of the respective volume pulse wave spectra of at least the first harmonic wave group to a third harmonic wave group.

11. The method according to claim 8, wherein the acquired maximum blood pressure value and the acquired minimum blood pressure value are a ratio of the maximum blood pressure value of the inspection target to the minimum blood pressure value of the inspection target.

12. The method according to claim 8, further comprising:
   estimating a blood vessel age of the inspection target on the basis of the viscoelastic characteristics.

13. A non-transitory computer-readable recording medium storing instructions, when executed by a computer, cause the computer to perform a method for acquiring viscoelastic characteristics of a blood vessel of an inspection target, the method causing the computer to execute:
   acquiring a time waveform corresponding to a volume pulse wave of the inspection target;
   performing Fourier transform on the time waveform and acquiring a volume pulse wave spectrum;
   acquire acquiring a maximum blood pressure value of the inspection target and a minimum blood pressure acquire value of the inspection target;
   calculating the viscoelastic characteristics on the basis of the acquired maximum blood pressure value, the acquired minimum blood pressure value, and the volume pulse wave spectrum at frequency bands equal to or higher than a frequency corresponding to a pulse of the inspection target;
   correcting a time waveform corresponding to a volume pulse wave on the basis of the viscoelastic characteristics; and
   estimating, in real time, a blood pressure waveform of the inspection target on the basis of the time waveform.

* * * * *